US009717802B2

(12) United States Patent
Binz

(10) Patent No.: US 9,717,802 B2
(45) Date of Patent: Aug. 1, 2017

(54) CAPPING MODULES FOR DESIGNED ANKYRIN REPEAT PROTEINS

(71) Applicant: Molecular Partners AG, Schlieren (CH)

(72) Inventor: Hans Kaspar Binz, Birmensdorf (CH)

(73) Assignee: Molecular Partners AG, Schlieren (CH)

( * ) Notice: Subject to any disclaimer, the term of this patent is extended or adjusted under 35 U.S.C. 154(b) by 0 days.

(21) Appl. No.: 14/947,148

(22) Filed: Nov. 20, 2015

(65) Prior Publication Data

US 2016/0075767 A1  Mar. 17, 2016

Related U.S. Application Data

(63) Continuation of application No. 13/989,181, filed as application No. PCT/EP2011/071084 on Nov. 25, 2011, now Pat. No. 9,221,892.

(30) Foreign Application Priority Data

Nov. 26, 2010  (EP) .................................. 10192711

(51) Int. Cl.
| A61K 47/48 | (2006.01) |
| C07K 14/47 | (2006.01) |
| C07K 14/00 | (2006.01) |
| C07K 16/00 | (2006.01) |
| A61K 38/00 | (2006.01) |

(52) U.S. Cl.
CPC ...... *A61K 47/48246* (2013.01); *C07K 14/001* (2013.01); *C07K 14/47* (2013.01); *C07K 14/4702* (2013.01); *C07K 16/00* (2013.01); *A61K 38/00* (2013.01); *C07K 2318/20* (2013.01); *C07K 2319/00* (2013.01); *C07K 2319/21* (2013.01); *C07K 2319/22* (2013.01); *C07K 2319/30* (2013.01); *C07K 2319/31* (2013.01); *C07K 2319/55* (2013.01); *C07K 2319/60* (2013.01)

(58) Field of Classification Search
None
See application file for complete search history.

(56) References Cited

U.S. PATENT DOCUMENTS

| 7,417,130 | B2 | 8/2008 | Stumpp et al. |
| 8,110,653 | B2 | 2/2012 | Stumpp et al. |
| 8,710,187 | B2 | 4/2014 | Binz et al. |
| 8,722,618 | B2 | 5/2014 | Jacobs et al. |
| 8,846,577 | B2 | 9/2014 | Steiner et al. |
| 8,901,076 | B2 | 12/2014 | Binz et al. |
| 2011/0224100 | A1 | 9/2011 | Parmeggiani et al. |
| 2012/0142611 | A1 | 6/2012 | Stumpp et al. |
| 2013/0244940 | A1 | 9/2013 | Steiner et al. |
| 2014/0005125 | A1 | 1/2014 | Baumann |
| 2014/0206599 | A1 | 7/2014 | Baumann et al. |
| 2014/0221295 | A1 | 8/2014 | Binz et al. |
| 2015/0057186 | A1 | 2/2015 | Steiner et al. |

FOREIGN PATENT DOCUMENTS

| WO | WO 2008/043822 A2 | 4/2008 |
| WO | WO 2009/115919 A2 | 9/2009 |
| WO | WO 2010/060748 A1 | 6/2010 |

OTHER PUBLICATIONS

GenBank Accession No. AB188512.1, "Gallus gallus mRNA for transcription factor GA binding protein, beta subunit, complete cds," Sep. 17, 2005.
Toku et al., "Isolation and characterization of chicken GA-binding protein," Biochimica et Biophysica Acta, vol. 1579, pp. 50-54 (2002).
International Search Report issued May 10, 2012 in International (PCT) Application No. PCT/EP2011/071084.
Sennhauser and Grutter., "Chaperone-Assisted Crystallography with DARPins", Structure (2008) vol. 16, pp. 1443-1453.
Steiner et al., "Efficient Selection of DARPins with Sub-nanomolar Affinities using SRP Phage Display", J Mol Biol (2008), vol. 382, No. 5, pp. 1211-1227 (incl.Supplement).
Stumpp et al, "DARPins: A new generation of protein therapeutics", Drug Discovery Today, vol. 00, pp. 1-7, (2008).
Veesler et al., "Crystal Structure and Function of DARPin Neutralizing Inhibitor of Lactococcal Phage TP901-1", J Biol Chem (2009), vol. 284, No. 44, pp. 30718-30726.
Eggel et al., "DARPins as Bispecific Receptor Antagonists Analyzed for Immunoglobulin E. Receptor Blockage", J Mol Biol (2009) vol. 393, pp. 598-607.
Kramer et al., Structural Determinants for Improved Stability of Designed Ankyrin Repeat Proteins with a Redesigned C-Capping Module, J Mol Biol, (2010) vol. 404, pp. 381-391.
Theurillat et al., "Designed ankyrin repeat proteins: a novel tool for testing epidermal growth factor receptor 2 expression in breast cancer," Modern Pathology (2010), pp. 1-9.
Zahnd et al., "Efficient Tumor Targeting with High-Affinity Designed Ankyrin Repeat Proteins: Effects of Affinity and Molecular Size", Cancer Res (2010) vol. 70, No. 4, pp. 1595-1605 (incl. Supplement).
Zahnd et al., "Ribosome display: selecting and evolving proteins in vitro that specifically bind to a target," Nature Methods (2007) vol. 4, No. 3, pp. 269-279.
Binz et al., "Designing Repeat Proteins: Well-expressed, Soluble and Stable Proteins from Combinatorial Libraries of Consensus Ankyrin Repeat Proteins" J Mol Biol (2003) vol. 332, pp. 489-503.
Forrer et al., "A novel strategy to design binging molecules harnessing the modular nature of repeat proteins," FEBS Letters (2003) vol. 539, pp. 2-6.
Stumpp et al., "Designing Repeat Proteins: Modular Leucine-rich Repeat Protein Libraries Based on the Mammalian Ribonuclease Inhibitor Family", J Mol Biol (2003) vol. 332, pp. 471-487.

(Continued)

*Primary Examiner* — Christina Bradley
(74) *Attorney, Agent, or Firm* — Finnegan, Henderson, Farabow, Garrett & Dunner LLP

(57) ABSTRACT

Improved N-terminal capping modules for designed Ankyrin repeat proteins (DARPins) conferring improved thermal stability to the DARPins are described, as well as nucleic acids encoding such proteins, pharmaceutical compositions comprising such proteins and the use of such proteins in the treatment of diseases.

22 Claims, 2 Drawing Sheets

(56) References Cited

OTHER PUBLICATIONS

Kohl et al., "Designed to be stable: Crystal structure of a consensus ankyrin repeat protein", PNAS (2003) vol. 100, No. 4, pp. 1700-1705.
Amstutz et al., "Intracellular Kinase Inhibitors Selected from Combinatorial Libraries of Designed Ankyrin Repeat Proteins", JBC (2005) vol. 280 No. 26, pp. 24715-24722.
He and Taussig., "Ribosome display: Cell-free protein display technology," Brief Funct Genomic Proteomic (2002) vol. 1, No. 2, pp. 204-212.
Hanes and Pluckthun., "In vitro selection and evolution of functional proteins by using ribosome display," Proc Natl Acad Sci USA (1997) vol. 94, No. 10, pp. 4937-4942.
Stumpp and Amstutz., "DARPins: A true alternative to antibodies," Curr Opin Drug Discov Devel. (2007) vol. 10, No. 2, pp. 153-159.
Interlandi et al., "Characterization and Further Stabilization of Designed Ankyrin Repeat Proteins by Combining Molecular Dynamics Simulations and Experiments," J Mol Biol (2008) vol. 375, No. 3, pp. 837-854.
Zahnd et al., "A designed ankyrin repeat protein evolved to picomolar affinity to Her2," J Mol Biol (2007) vol. 369, No. 4, pp. 1015-1028.
Forrer et al., "Consensus Design of Repeat Proteins," ChemBioChem (2004) vol. 5, pp. 183-189.
Binz et al., "Designed Repeat Proteins—Molecules with Antibody-like Binding Properties," BIOforum Europe (2005), pp. 34-36, Git Verlag GmbH & Co. KG, Darmstadt.
Binz et al., "Engineered proteins as specific binding reagents," Current Opinion in Biotechnology (2005) vol. 16, pp. 459-469.
Binz et al., "Engineering novel binding proteins from nonimmunoglobulin domains," Nature Biotechnology (2005) vol. 23, No. 10, pp. 1257-1268.
Amstutz et al., "Rapid selection of specific MAP kinase-binders from designed ankyrin repeat protein libraries," Protein Engineering, Design & Selection (2006) vol. 19, No. 5, pp. 219-229.
Binz et al., "Crystal Structure of a Consensus-Designed Ankyrin Repeat Protein: Implications for Stability," Proteins: Structure, Function, and Bioinformatics, (2006) vol. 65, pp. 280-284.
Kawe et al., "Isolation of Intracellular Proteinase Inhibitors Derived from Designed Ankyrin Repeat Proteins by Genetic Screening," J Biol Chem (2006) vol. 281(52), pp. 40252-40263.
Zahnd et al., "Selection and Characterization of Her2 Binding-designed Ankyrin Repeat Proteins," J Biol Chem (2006) vol. 281, No. 46, pp. 35167-35175.
Boersma and Pluckthun, "DARPins and other repeat protein scaffolds: advances in engineering and applications," Curr Opin Biotechnol (2011) vol. 22, No. 6, pp. 849-857.
GenBank: BAD89995.1 "Transcription factor GA binding protein, beta subunit [Gallus gallus]" Sep. 17, 2005.
Binz, et al. "High-affinity binders selected from designed ankyrin repeat protein libraries" Nature Biotechnology, vol. 22 No. 5, May 2004, p. 575-582.
Binz "High-affinity binders selected from designed ankyrin repeat protein libraries" Nature Biotechnology. vol. 22 No. 5, May 2004, p. 575-582.
Binz et al., "Designed Repeat Proteins-Molecules with Antibody-like Binding Properties," BIOforum Europe (2005), pp. 34-36, Git Verlag GmbH & Co. KG, Darmstadt.
Binz, "Designing Repeat Proteins: Well-expressed, Soluble and Stable Proteins from Combinatorial Libraries of Consensus Ankyrin Repeat Proteins" J Mol Biol (2003) vol. 332, pp. 489-503.
Boersma et al., "DARPins and other repeat protein scaffolds: advances in engineering and applications," Curr Opin Biotechnol (2011) vol. 22, No. 6, pp. 849-857.
Eggel et al., "DARPins as Bispecific Receptor Antagonists Analyzed for Immunoglobulin E Receptor Blockage", J Mol Biol (2009) vol. 393, pp. 598-607.
Forrer et al., "A novel strategy to design binding molecules harnessing the modular nature of repeat proteins," FEBS Letters (2003) vol. 539, pp. 2-6.
Hanes et al., "In vitro selection and evolution of functional proteins by using ribosome display," Proc Natl Acad Sci USA (1997) vol. 94, No. 10, pp. 4937-4942.
He et al., "Ribosome display: Cell-free protein display technology," Brief Funct Genomic Proteomic (2002) vol. 1, No. 2, pp. 204-212.
International Search Report issued May 10, 2012 in International (PCT) Application No. PCT/EP2011/071084.
Kawe et al., "Isolation of Intracellular Proteinase Inhibitors Derived from Designed Ankyrin Repeat Proteins by Genetic Screening," J Biol Chern (2006) vol. 281, pp. 40252-40263.
Kramer et al., "Structural Determinants for Improved Stability of Designed Ankyrin Repeat Proteins with a Redesigned C- Capping Module", J Mol Biol, (2010) vol. 404, pp. 381-391.
Sennhauser et al., "Chaperone-Assisted Crystallography with DARPins", Structure (2008) vol. 16, pp. 1443-1453.
Steiner et al., "Efficient Selection of DARPins with Sub-nanomolar Affinities using SRP Phage Display", J Mol Biol (2008), vol. 382, No. 5, pp. 1211-1227 (incl. Supplement).
Stumpp et al., "DARPins: A new generation of protein therapeutics", Drug Discovery Today, vol. 00, pp. 1-7, (2008).
Stumpp et al., "DARPins: A true alternative to antibodies," Curr Opin Drug Discov Devel. (2007) vol. 10, No. 2, pp. 153-159.
Theurillat et al., "Designed ankyrin repeat proteins: a novel tool for testing epidermal growth factor receptor 2 expression in breast cancer", Modern Pathology (2010), pp. 1-9.
Veesler et al., "Crystal Structure and Function of a DARPin Neutralizing Inhibitor of Lactococcal Phage TP901-1", J Biol Chern (2009), vol. 284, No. 44, pp. 30718-30726.
Bandeiras, T.M., et al., "Structure of wild-type Plk-1 kinase domain in complex with a selective DARPin," *Acta Cryst.* (2008) D64, 339-353.
GenBank PDB: 2V5Q_C "Chain C, Crystal Structure of Wild-type Plk-1 Kinase Domain in Complex With a Selective Darpin," release date: Jan. 25, 2013; accessed Sep. 19, 2016 (3 pages).
GenBank PDB: 2V5Q_D "Chain D, Crystal Structure of Wild-type Plk-1 Kinase Domain in Complex With a Selective Darpin," release date: Jan. 25, 2013; accessed Oct. 25, 2016 (3 pages).

SEQUENCE LISTING

```
<160> NUMBER OF SEQ ID NOS: 32

<210> SEQ ID NO 1
<211> LENGTH: 32
<212> TYPE: PRT
<213> ORGANISM: Artificial Sequence
<220> FEATURE:
<223> OTHER INFORMATION: Synthetic Construct

<400> SEQUENCE: 1

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

<210> SEQ ID NO 2
<211> LENGTH: 28
<212> TYPE: PRT
<213> ORGANISM: Artificial Sequence
<220> FEATURE:
<223> OTHER INFORMATION: Synthetic Construct

<400> SEQUENCE: 2

Gln Asp Lys Phe Gly Lys Thr Ala Phe Asp Ile Ser Ile Asp Asn Gly
1               5                   10                  15

Asn Glu Asp Leu Ala Glu Ile Leu Gln Lys Leu Asn
```

```
                        20                  25

<210> SEQ ID NO 3
<211> LENGTH: 28
<212> TYPE: PRT
<213> ORGANISM: Artificial Sequence
<220> FEATURE:
<223> OTHER INFORMATION: Synthetic Construct

<400> SEQUENCE: 3

Gln Asp Lys Phe Gly Lys Thr Pro Phe Asp Leu Ala Ile Arg Glu Gly
1               5                   10                  15

His Glu Asp Ile Ala Glu Val Leu Gln Lys Ala Ala
            20                  25

<210> SEQ ID NO 4
<211> LENGTH: 28
<212> TYPE: PRT
<213> ORGANISM: Artificial Sequence
<220> FEATURE:
<223> OTHER INFORMATION: Synthetic Construct

<400> SEQUENCE: 4

Gln Asp Lys Phe Gly Lys Thr Pro Phe Asp Leu Ala Ile Asp Asn Gly
1               5                   10                  15

Asn Glu Asp Ile Ala Glu Val Leu Gln Lys Ala Ala
            20                  25

<210> SEQ ID NO 5
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (24)..(26)
<223> OTHER INFORMATION: Xaa can be any naturally occurring amino acid

<400> SEQUENCE: 5

Gly Ser Xaa Leu Xaa Lys Lys Leu Leu Glu Ala Ala Arg Ala Gly Gln
1               5                   10                  15

Asp Asp Glu Val Xaa Xaa Leu Xaa Xaa Xaa Gly Ala Asp Val Asn Ala
            20                  25                  30

<210> SEQ ID NO 6
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
```

```
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 6

Xaa Asp Lys Xaa Gly Lys Thr Xaa Xaa Asp Xaa Xaa Xaa Asp Xaa Gly
1               5                   10                  15

Xaa Glu Asp Xaa Ala Glu Xaa Leu Gln Lys Ala Ala
            20                  25

<210> SEQ ID NO 7
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 7

Xaa Asp Lys Xaa Gly Lys Thr Xaa Ala Asp Xaa Xaa Xaa Asp Xaa Gly
1               5                   10                  15
```

```
Xaa Glu Asp Xaa Ala Glu Xaa Leu Gln Lys Ala Ala
            20                  25

<210> SEQ ID NO 8
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 8

Xaa Asp Lys Xaa Gly Lys Thr Xaa Ala Asp Xaa Xaa Ala Asp Xaa Gly
1               5                   10                  15

Xaa Glu Asp Xaa Ala Glu Xaa Leu Gln Lys Ala Ala
            20                  25

<210> SEQ ID NO 9
<211> LENGTH: 28
<212> TYPE: PRT
<213> ORGANISM: Artificial Sequence
<220> FEATURE:
<223> OTHER INFORMATION: Synthetic Construct

<400> SEQUENCE: 9

Gln Asp Lys Ser Gly Lys Thr Pro Ala Asp Leu Ala Ala Asp Ala Gly
1               5                   10                  15

His Glu Asp Ile Ala Glu Val Leu Gln Lys Ala Ala
            20                  25

<210> SEQ ID NO 10
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
```

```
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 10

Xaa Asp Xaa Xaa Gly Xaa Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 11
<211> LENGTH: 6
<212> TYPE: PRT
<213> ORGANISM: Artificial Sequence
<220> FEATURE:
<223> OTHER INFORMATION: Synthetic Construct

<400> SEQUENCE: 11

Arg Ile Leu Leu Lys Ala
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct

<400> SEQUENCE: 12

Arg Glu Leu Leu Lys Ala
1               5

<210> SEQ ID NO 13
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 13
```

```
Xaa Leu Xaa Lys Lys Leu Leu Glu Ala Ala Arg Ala Gly Gln Asp Asp
1               5                   10                  15

Glu Val Arg Ile Leu Xaa Ala Xaa Gly Ala Asp Val Asn Ala
            20              25                  30

<210> SEQ ID NO 14
<211> LENGTH: 32
<212> TYPE: PRT
<213> ORGANISM: Artificial Sequence
<220> FEATURE:
<223> OTHER INFORMATION: Synthetic Construct

<400> SEQUENCE: 14

Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Synthetic Construct

<400> SEQUENCE: 15

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Met Arg Gly Ser His His His His His His
1               5                   10

<210> SEQ ID NO 17
<211> LENGTH: 126
<212> TYPE: PRT
<213> ORGANISM: Artificial Sequence
<220> FEATURE:
<223> OTHER INFORMATION: Synthetic Construct

<400> SEQUENCE: 17

Gly Ser Asp Leu Gly Lys Lys Leu Leu Glu Ala Ala Arg Ala Gly Gln
1               5                   10                  15

Asp Asp Glu Val Arg Ile Leu Met Lys Ala Gly Ala Asp Val Asn Ala
            20                  25                  30

Lys Asp Glu Tyr Gly Leu Thr Pro Leu Tyr Leu Ala Thr Ala His Gly
            35                  40                  45

His Leu Glu Ile Val Glu Val Leu Leu Lys Asn Gly Ala Asp Val Asn
        50                  55                  60

Ala Val Asp Ala Ile Gly Phe Thr Pro Leu His Leu Ala Ala Phe Ile
65                  70                  75                  80

Gly His Leu Glu Ile Ala Glu Val Leu Leu Lys His Gly Ala Asp Val
                85                  90                  95
```

Asn Ala Gln Asp Lys Phe Gly Lys Thr Ala Phe Asp Ile Ser Ile Gly
            100                 105                 110

Asn Gly Asn Glu Asp Leu Ala Glu Ile Leu Gln Lys Leu Asn
        115                 120                 125

<210> SEQ ID NO 18
<211> LENGTH: 126
<212> TYPE: PRT
<213> ORGANISM: Artificial Sequence
<220> FEATURE:
<223> OTHER INFORMATION: Synthetic Construct

<400> SEQUENCE: 18

Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
            20                  25                  30

Lys Asp Glu Tyr Gly Leu Thr Pro Leu Tyr Leu Ala Thr Ala His Gly
        35                  40                  45

His Leu Glu Ile Val Glu Val Leu Leu Lys Asn Gly Ala Asp Val Asn
    50                  55                  60

Ala Val Asp Ala Ile Gly Phe Thr Pro Leu His Leu Ala Ala Phe Ile
65                  70                  75                  80

Gly His Leu Glu Ile Ala Glu Val Leu Leu Lys His Gly Ala Asp Val
                85                  90                  95

Asn Ala Gln Asp Lys Phe Gly Lys Thr Ala Phe Asp Ile Ser Ile Gly
            100                 105                 110

Asn Gly Asn Glu Asp Leu Ala Glu Ile Leu Gln Lys Leu Asn
        115                 120                 125

<210> SEQ ID NO 19
<211> LENGTH: 159
<212> TYPE: PRT
<213> ORGANISM: Artificial Sequence
<220> FEATURE:
<223> OTHER INFORMATION: Synthetic Construct

<400> SEQUENCE: 19

Gly Ser Asp Leu Gly Lys Lys Leu Leu Glu Ala Ala Arg Ala Gly Gln
1               5                   10                  15

Asp Asp Glu Val Arg Ile Leu Met Lys Ala Gly Ala Asp Val Asn Ala
            20                  25                  30

Phe Asp Trp Met Gly Trp Thr Pro Leu His Leu Ala Ala His Glu Gly
        35                  40                  45

His Leu Glu Ile Val Glu Val Leu Leu Lys Asn Gly Ala Asp Val Asn
    50                  55                  60

Ala Thr Asp Val Ser Gly Tyr Thr Pro Leu His Leu Ala Ala Ala Asp
65                  70                  75                  80

Gly His Leu Glu Ile Val Glu Val Leu Leu Lys His Gly Ala Asp Val
                85                  90                  95

Asn Thr Lys Asp Asn Thr Gly Trp Thr Pro Leu His Leu Ser Ala Asp
            100                 105                 110

Leu Gly His Leu Glu Ile Val Glu Val Leu Leu Lys Asn Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 20
<211> LENGTH: 159
<212> TYPE: PRT
<213> ORGANISM: Artificial Sequence
<220> FEATURE:
<223> OTHER INFORMATION: Synthetic Construct

<400> SEQUENCE: 20

```
Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
                20                  25                  30

Phe Asp Trp Met Gly Trp Thr Pro Leu His Leu Ala Ala His Glu Gly
            35                  40                  45

His Leu Glu Ile Val Glu Val Leu Leu Lys Asn Gly Ala Asp Val Asn
    50                  55                  60

Ala Thr Asp Val Ser Gly Tyr Thr Pro Leu His Leu Ala Ala Ala Asp
65                  70                  75                  80

Gly His Leu Glu Ile Val Glu Val Leu Leu Lys His Gly Ala Asp Val
                85                  90                  95

Asn Thr Lys Asp Asn Thr Gly Trp Thr Pro Leu His Leu Ser Ala Asp
                100                 105                 110

Leu Gly His Leu Glu Ile Val Glu Val Leu Leu Lys Asn Gly Ala Asp
            115                 120                 125

Val Asn Ala Gln Asp Lys Phe Gly Lys Thr Ala Phe Asp Ile Ser Ile
        130                 135                 140

Asp Asn Gly Asn Glu Asp Leu Ala Glu Ile Leu Gln Lys Leu Asn
145                 150                 155
```

<210> SEQ ID NO 21
<211> LENGTH: 93
<212> TYPE: PRT
<213> ORGANISM: Artificial Sequence
<220> FEATURE:
<223> OTHER INFORMATION: Synthetic Construct

<400> SEQUENCE: 21

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Lys Asp Lys Asp Gly Tyr Thr Pro Leu His Leu Ala Ala Arg Glu Gly
            35                  40                  45

His Leu Glu Ile Val Glu Val Leu Leu Lys Ala Gly Ala Asp Val Asn
    50                  55                  60

Ala Gln Asp Lys Phe Gly Lys Thr Ala Phe Asp Ile Ser Ile Asp Asn
65                  70                  75                  80

Gly Asn Glu Asp Leu Ala Glu Ile Leu Gln Lys Leu Asn
                85                  90
```

<210> SEQ ID NO 22
<211> LENGTH: 93
<212> TYPE: PRT
<213> ORGANISM: Artificial Sequence
<220> FEATURE:
<223> OTHER INFORMATION: Synthetic Construct

<400> SEQUENCE: 22

Gly Ser Asp Leu Gly Lys Lys Leu Leu Glu Ala Ala Arg Ala Gly Gln
1               5                   10                  15

Asp Asp Glu Val Arg Ile Leu Ala Ala Gly Ala Asp Val Asn Ala
            20                  25                  30

Lys Asp Lys Asp Gly Tyr Thr Pro Leu His Leu Ala Ala Arg Glu Gly
        35                  40                  45

His Leu Glu Ile Val Glu Val Leu Leu Lys Ala Gly Ala Asp Val Asn
    50                  55                  60

Ala Gln Asp Lys Phe Gly Lys Thr Ala Phe Asp Ile Ser Ile Asp Asn
65                  70                  75                  80

Gly Asn Glu Asp Leu Ala Glu Ile Leu Gln Lys Leu Asn
                85                  90

<210> SEQ ID NO 23
<211> LENGTH: 93
<212> TYPE: PRT
<213> ORGANISM: Artificial Sequence
<220> FEATURE:
<223> OTHER INFORMATION: Synthetic Construct

<400> SEQUENCE: 23

Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
            20                  25                  30

Lys Asp Lys Asp Gly Tyr Thr Pro Leu His Leu Ala Ala Arg Glu Gly
        35                  40                  45

His Leu Glu Ile Val Glu Val Leu Leu Lys Ala Gly Ala Asp Val Asn
    50                  55                  60

Ala Gln Asp Lys Phe Gly Lys Thr Ala Phe Asp Ile Ser Ile Asp Asn
65                  70                  75                  80

Gly Asn Glu Asp Leu Ala Glu Ile Leu Gln Lys Leu Asn
                85                  90

<210> SEQ ID NO 24
<211> LENGTH: 126
<212> TYPE: PRT
<213> ORGANISM: Artificial Sequence
<220> FEATURE:
<223> OTHER INFORMATION: Synthetic Construct

<400> SEQUENCE: 24

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Leu Asn
        115                 120                 125

<210> SEQ ID NO 25
<211> LENGTH: 126
<212> TYPE: PRT
<213> ORGANISM: Artificial Sequence
<220> FEATURE:
<223> OTHER INFORMATION: Synthetic Construct

<400> SEQUENCE: 25

```
Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Leu Asn
        115                 120                 125
```

<210> SEQ ID NO 26
<211> LENGTH: 126
<212> TYPE: PRT
<213> ORGANISM: Artificial Sequence
<220> FEATURE:
<223> OTHER INFORMATION: Synthetic Construct

<400> SEQUENCE: 26

```
Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Leu Asn
        115                 120                 125
```

<210> SEQ ID NO 27
<211> LENGTH: 126
<212> TYPE: PRT
<213> ORGANISM: Artificial Sequence
<220> FEATURE:
<223> OTHER INFORMATION: Artificial Sequence

<400> SEQUENCE: 27

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ala Asp Tyr Phe Ser His Thr Pro Leu His Leu Ala Ala Arg Asn Gly
        35                  40                  45

His Leu Lys Ile Val Glu Val Leu Leu Lys Tyr Gly Ala Asp Val Asn
    50                  55                  60

Ala Ser Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Ile Phe Gly Lys Thr Ala Phe Asp Ile Ser Ile Asp
            100                 105                 110

Asn Gly Asn Glu Asp Leu Ala Glu Ile Leu Gln Lys Leu Asn
            115                 120                 125

<210> SEQ ID NO 28
<211> LENGTH: 126
<212> TYPE: PRT
<213> ORGANISM: Artificial Sequence
<220> FEATURE:
<223> OTHER INFORMATION: Synthetic Construct

<400> SEQUENCE: 28

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ala Asp Tyr Phe Ser His Thr Pro Leu His Leu Ala Ala Arg Asn Gly
        35                  40                  45

His Leu Lys Ile Val Glu Val Leu Leu Lys Tyr Gly Ala Asp Val Asn
    50                  55                  60

Ala Ser Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Ile Phe Gly Lys Thr Pro Ala Asp Ile Ala Ala Asp
            100                 105                 110

Asn Gly His Glu Asp Ile Ala Glu Val Leu Gln Lys Leu Asn
            115                 120                 125

<210> SEQ ID NO 29
<211> LENGTH: 126
<212> TYPE: PRT
<213> ORGANISM: Artificial Sequence
<220> FEATURE:
<223> OTHER INFORMATION: Synthetic Construct

<400> SEQUENCE: 29

Gly Ser Asp Leu Gly Lys Lys Leu Leu Glu Ala Ala Arg Ala Gly Gln
1               5                   10                  15

Asp Asp Glu Val Arg Ile Leu Leu Ala Ala Gly Ala Asp Val Asn Ala
            20                  25                  30

Ala Asp Glu Arg Gly Thr Thr Pro Leu His Leu Ala Ala Val Tyr Gly
        35                  40                  45

His Leu Glu Ile Val Glu Val Leu Leu Lys Asn Gly Ala Asp Val Asn
    50                  55                  60

```
Ala Gln Asn Glu Thr Gly Tyr Thr Pro Leu His Leu Ala Asp Ser Ser
 65                  70                  75                  80

Gly His Leu Glu Ile Val Glu Val Leu Leu Lys His Ser Ala Asp Val
                 85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Leu Asn
        115                 120                 125
```

<210> SEQ ID NO 30
<211> LENGTH: 126
<212> TYPE: PRT
<213> ORGANISM: Artificial Sequence
<220> FEATURE:
<223> OTHER INFORMATION: Synthetic Construct

<400> SEQUENCE: 30

```
Gly Ser Asp Leu Gly Lys Lys Leu Leu Glu Ala Ala Arg Ala Gly Gln
1               5                   10                  15

Asp Asp Glu Val Arg Ile Leu Leu Ala Ala Gly Ala Asp Val Asn Ala
                20                  25                  30

Ala Asp Glu Arg Gly Thr Thr Pro Leu His Leu Ala Ala Val Tyr Gly
            35                  40                  45

His Leu Glu Ile Val Glu Val Leu Leu Lys Asn Gly Ala Asp Val Asn
        50                  55                  60

Ala Gln Asn Glu Thr Gly Tyr Thr Pro Leu His Leu Ala Asp Ser Ser
 65                  70                  75                  80

Gly His Leu Glu Ile Val Glu Val Leu Leu Lys His Ser Ala Asp Val
                 85                  90                  95

Asn Ala Gln Asp Lys Ser Gly Lys Thr Pro Ala Asp Ile Ala Ala Asp
            100                 105                 110

Asn Gly His Glu Asp Ile Ala Glu Val Leu Gln Lys Leu Asn
        115                 120                 125
```

<210> SEQ ID NO 31
<211> LENGTH: 103
<212> TYPE: PRT
<213> ORGANISM: Artificial Sequence
<220> FEATURE:
<223> OTHER INFORMATION: Synthetic Construct

<400> SEQUENCE: 31

```
Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
                20                  25                  30

Leu Met Ala Asn Gly Ala Asp Val Asn Ala Lys Asp Lys Asp Gly Tyr
            35                  40                  45

Thr Pro Leu His Leu Ala Ala Arg Glu Gly His Leu Glu Ile Val Glu
        50                  55                  60

Val Leu Leu Lys Ala Gly Ala Asp Val Asn Ala Gln Asp Lys Phe Gly
 65                  70                  75                  80

Lys Thr Ala Phe Asp Ile Ser Ile Asp Asn Gly Asn Glu Asp Leu Ala
                 85                  90                  95

Glu Ile Leu Gln Lys Leu Asn
            100
```

```
<210> SEQ ID NO 32
<211> LENGTH: 103
<212> TYPE: PRT
<213> ORGANISM: Artificial Sequence
<220> FEATURE:
<223> OTHER INFORMATION: Synthetic Construct

<400> SEQUENCE: 32

Met Arg Gly Ser His His His His His Gly Ser Asp Leu Gly Lys
1               5                   10                  15

Lys Leu Leu Glu Ala Ala Arg Ala Gly Gln Asp Asp Glu Val Arg Ile
                20                  25                  30

Leu Met Ala Asn Gly Ala Asp Val Asn Ala Lys Asp Lys Asp Gly Tyr
            35                  40                  45

Thr Pro Leu His Leu Ala Ala Arg Glu Gly His Leu Glu Ile Val Glu
        50                  55                  60

Val Leu Leu Lys Ala Gly Ala Asp Val Asn Ala Gln Asp Lys Ser Gly
65                  70                  75                  80

Lys Thr Pro Ala Asp Leu Ala Ala Asp Asn Gly His Glu Asp Ile Ala
                85                  90                  95

Glu Val Leu Gln Lys Ala Ala
            100
```

CAPPING MODULES FOR DESIGNED ANKYRIN REPEAT PROTEINS

This application is a continuation of U.S. application Ser. No. 13/989,181, filed Jun. 27, 2013, which is the U.S. national stage application of International Application No. PCT/EP/2011/071084 filed Nov. 25, 2011, which claims the benefit of priority of European Application No. 10192711.9 filed Nov. 26, 2010, all of which are incorporated herein by reference.

FIELD OF THE INVENTION

The present invention relates to improved N-terminal capping modules for designed ankyrin repeat proteins (DARPins) conferring improved thermal stability to the DARPins, as well as nucleic acids encoding such proteins, pharmaceutical compositions comprising such proteins and the use of such proteins in the treatment of diseases.

BACKGROUND OF THE INVENTION

There are, beside antibodies, novel binding proteins or binding domains that can be used to specifically bind a target molecule (e.g. Binz, H. K., Amstutz, P. and Plückthun, A., Nat. Biotechnol. 23, 1257-1268, 2005). One such novel class of binding proteins or binding domains are based on designed repeat proteins or designed repeat domains (WO 2002/020565; Binz, H. K., Amstutz, P., Kohl, A., Stumpp, M. T., Briand, C., Forrer, P., Grütter, M. G., and Plückthun, A., Nat Biotechnol. 22, 575-582, 2004; Stumpp, M. T., Binz, H. K and Amstutz, P., Drug Discov. Today 13, 695-701, 2008). WO 2002/020565 describes how large libraries of repeat proteins can be constructed and their general application. These designed repeat domains harness the modular nature of repeat proteins and possess N-terminal and C-terminal capping modules to prevent the designed repeat domains from aggregation by shielding the hydrophobic core of the domain (Forrer, P., Stumpp, M. T., Binz. H. K., and Plückthun, A., FEBS letters 539, 2-6, 2003). These capping modules were based on the capping repeats of the natural guanine-adenine-binding protein (GA-binding protein). It was shown that the thermal and thermodynamic stability of these designed ankyrin repeat domains could be further increased by improving the C-terminal capping repeat derived from the GA-binding protein (Interlandi, G., Wetzel, S. K, Settanni, G., Plückthun, A. and Caflisch, A., J. Mol. Biol 375, 837-854, 2008; Kramer, M. A, Wetzel, S. K., Plückthun, A., Mittl, P. R. E, and Grütter, M. G., J. Mol. Biol. 404, 381-391, 2010). The authors introduced a total of eight mutations into this capping module and extended its C-terminal helix by adding three distinct amino acids. Nevertheless, the introduction of these modifications in the C-terminal capping module resulted in a tendency of unwanted dimerization of a designed repeat domain carrying this mutated C-terminal capping module. Thus, there is a need for the generation of further optimized repeat proteins by improving the C- or N-terminal capping modules or C- or N-terminal capping repeats of designed ankyrin repeat domains.

Overall, a need exists for target-specific ankyrin repeat proteins with improved stability for treating cancer and other pathological conditions.

The technical problem underlying the present invention is identifying novel ankyrin repeat proteins with improved stability for an improved treatment of cancer and other pathological conditions. The solution to this technical problem is achieved by providing the embodiments characterized in the claims.

SUMMARY OF THE INVENTION

The present invention relates to a binding protein comprising at least one ankyrin repeat domain, wherein said ankyrin repeat domain comprises an N-terminal capping module having an amino acid sequence
GSDLGKKLLE AARAGQDDEV RILLKAGADV NA (SEQ ID NO:14) or
GSDLGKKLLE AARAGQDDEV RELLKAGADV NA (SEQ ID NO:15), wherein
the amino acid residue L at position 24 of SEQ ID NO:14 or SEQ ID NO:15 is optionally replaced by V, I or A;
up to 9 amino acids of SEQ ID NO:14 or SEQ ID NO:15 in other positions than position 24 are optionally exchanged by any amino acids; and
wherein G at position 1 and/or S at position 2 of SEQ ID NO:14 or SEQ ID NO:15 are optionally missing.

In particular the invention relates to a binding protein, wherein said N-terminal capping module comprises the sequence
GSX$_1$LX$_2$KKLLE AARAGQDDEV X$_3$X$_4$LX$_5$X$_6$X$_7$GADV NA (SEQ ID NO:5), wherein
G at position 1 and/or S at position 2 of SEQ ID NO:5 are optionally missing;
X$_1$ represents an amino acid residue G, A, or D;
X$_2$ represents an amino acid residue G or D;
X$_3$ represents an amino acid residue R or E;
X$_4$ represents an amino acid residue I, E or V;
X$_5$ represents an amino acid residue L, V, I or A;
X$_6$ represents an amino acid residue A, K or E; and
X$_7$ represents an amino acid residue selected from the group consisting of A, H, Y, K and R.

In another embodiment the invention relates to a binding protein comprising at least one ankyrin repeat domain, wherein said ankyrin repeat domain comprises an N-terminal capping module having an amino acid sequence with at least 70% amino acid sequence identity with
GSDLGKKLLE AARAGQDDEV RILLKAGADV NA (SEQ ID NO:14) or
GSDLGKKLLE AARAGQDDEV RELLKAGADV NA (SEQ ID NO:15), and with the condition that the amino acid residue in position 24 in the amino acid sequence of said N-terminal capping module is L, V, I or A;
and such N-terminal capping molecules wherein the amino acids in position 1 and/or 2 are missing.

Such binding proteins show improved thermal stability when compared to the same binding protein differing only in the N-terminal capping module, for example when compared to a binding protein with an N-terminal capping modules of the state of the art, such as an N-terminal capping module having an amino acid sequence with the amino acid M (methionine) in position 24, e.g. SEQ ID NO:14 or SEQ ID NO:15 wherein L at position 24 is replaced by M.

The invention further relates to a binding protein comprising at least one ankyrin repeat domain, wherein said ankyrin repeat domain comprises a C-terminal capping module having an amino acid sequence (SEQ ID NO: 6)
X$_1$DKX$_2$GKTX$_3$X$_4$DX$_5$X$_6$X$_7$DX$_8$GX$_9$EDX$_{10}$AEX$_{11}$LQKAA.

The invention further relates to nucleic acid molecules encoding the binding proteins of the present invention, and to a pharmaceutical composition comprising the above mentioned binding proteins or nucleic acid molecules.

The invention further relates to a method of treatment of a pathological condition using the binding proteins of the invention.

Traces from thermal denaturation of DARPin#17 and DARPin#18 are shown. The thermal denaturation is followed by an increase of the fluorescence intensity of the dye SYPRO orange present in PBS at pH 7.4. The Tm values for DARPin#17 and DARPin#18 were estimated to be 64.5° C. and 71.0° C., respectively.

F, relative fluorescence units (RFUs), excitation at 515-535 nm, detection at 560-580 nm; T, temperature in ° C.; Definition of DARPins see below.

Figure 2:
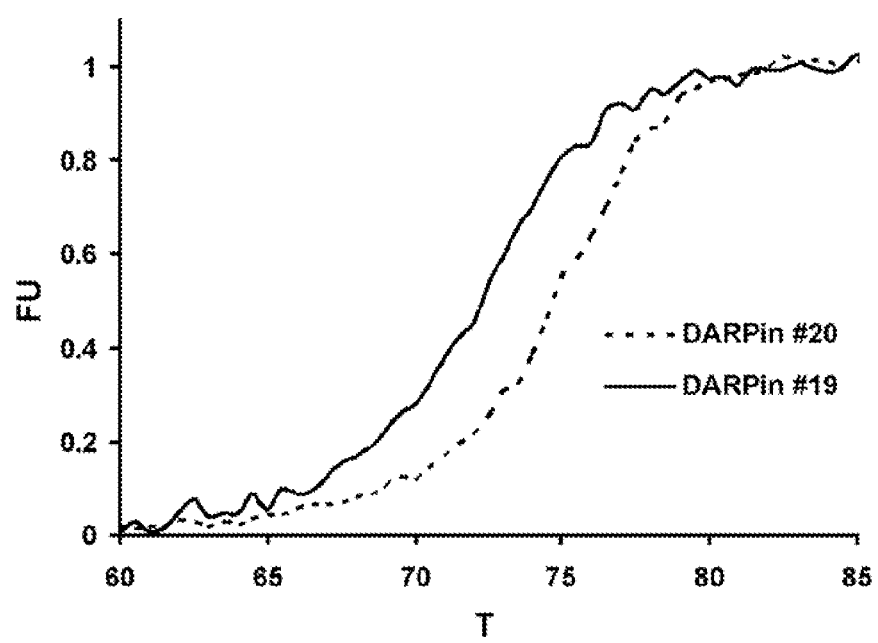

FIG. 2. Thermal stability of DARPin#19 and DARPin#20.

Traces from thermal denaturation of DARPin#19 and DARPin#20 are shown. The thermal denaturation is followed by the CD signal at 222 nm in PBS at pH 7.4. The Tm values for DARPin#19 and DARPin#20 were estimated to be 72.3° C. and 74.8° C., respectively.

FU, fraction unfolded; T, temperature in ° C.; Definition of DARPins see below.

Figure 3:
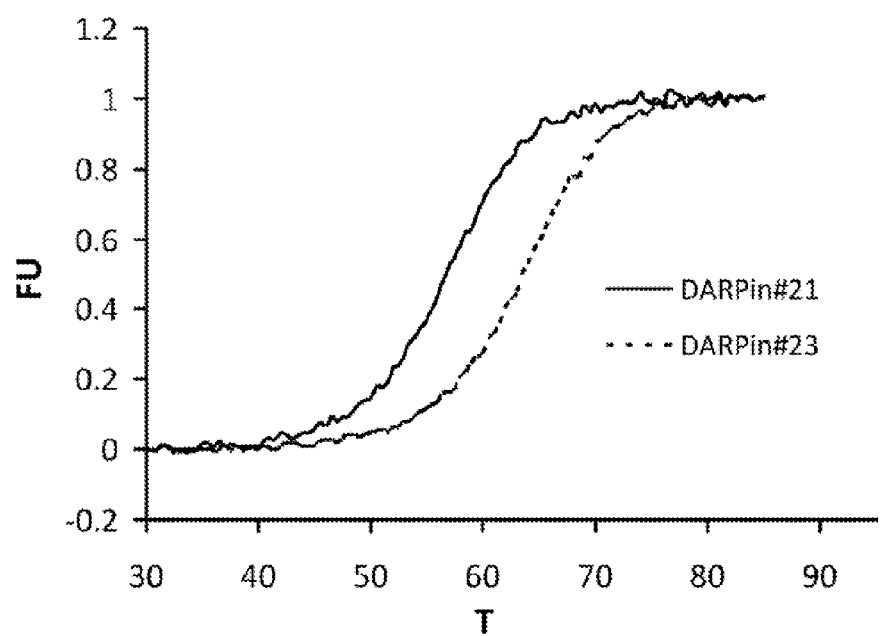

FIG. 3. Thermal stability of DARPin#21 and DARPin#23

Traces from thermal denaturation of DARPin#21 and DARPin#23 are shown. The thermal denaturation is followed by the CD signal at 222 nm in PBS at pH 7.4. The Tm values for DARPin#21 and DARPin#23 were estimated to be 56.5° C. and 63.5° C., respectively.

FU, fraction unfolded; T, temperature in ° C.; Definition of DARPins see below.

Figure 4:
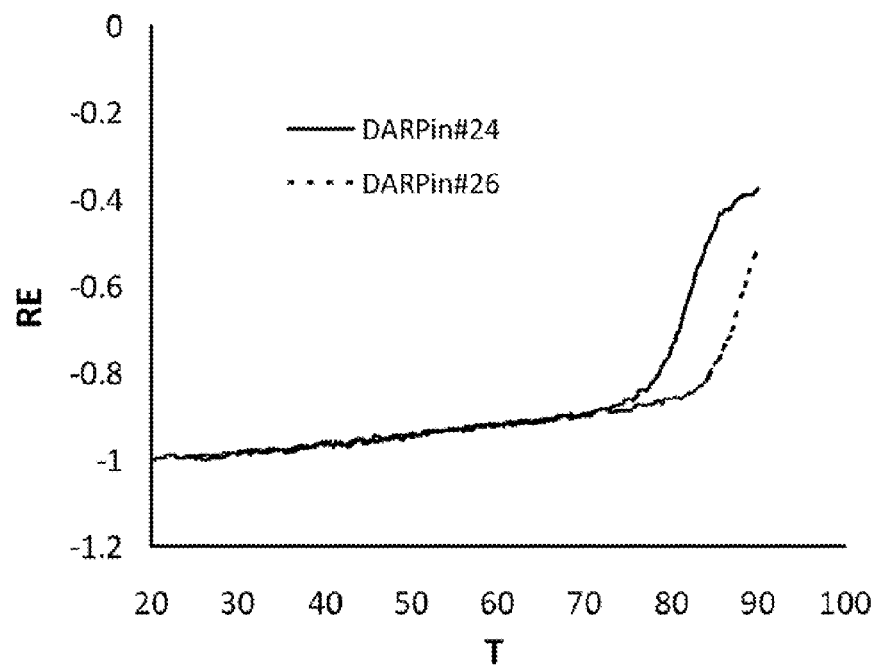

FIG. 4. Thermal stability of DARPin#24 and DARPin#26

Traces from thermal denaturation of DARPin#24 and DARPin#26 are shown. The thermal denaturation is followed by the CD signal at 222 nm in PBS at pH 7.4. The Tm values for DARPin#24 and DARPin#26 were estimated to be 83° C. and 89° C., respectively.

RE, relative CD signal at 222 nm normalized to the signal measured at 20° C.; T, temperature in ° C.; Definition of DARPins see below.

DETAILED DESCRIPTION OF THE INVENTION

The term "protein" refers to a polypeptide, wherein at least part of the polypeptide has, or is able to acquire a defined three-dimensional arrangement by forming secondary, tertiary, or quaternary structures within and/or between its polypeptide chain(s). If a protein comprises two or more polypeptides, the individual polypeptide chains may be linked non-covalently or covalently, e.g. by a disulfide bond between two polypeptides. A part of a protein, which individually has, or is able to acquire, a defined three-dimensional arrangement by forming secondary or tertiary structures, is termed "protein domain". Such protein domains are well known to the practitioner skilled in the art.

The term "recombinant" as used in recombinant protein, recombinant protein domain, recombinant binding protein and the like, means that said polypeptides are produced by the use of recombinant DNA technologies well known by the practitioner skilled in the relevant art. For example, a recombinant DNA molecule (e.g. produced by gene synthesis) encoding a polypeptide can be cloned into a bacterial expression plasmid (e.g. pQE30, Qiagen), yeast expression plasmid or mammalian expression plasmid. When, for example, such a constructed recombinant bacterial expression plasmid is inserted into an appropriate bacteria (e.g. *Escherichia coli*), this bacteria can produce the polypeptide encoded by this recombinant DNA. The correspondingly produced polypeptide is called a recombinant polypeptide.

In the context of the present invention, the term "polypeptide" relates to a molecule consisting of one or more chains of multiple, i.e. two or more, amino acids linked via peptide bonds. Preferably, a polypeptide consists of more than eight amino acids linked via peptide bonds.

The term "polypeptide tag" refers to an amino acid sequence attached to a polypeptide/protein, wherein said amino acid sequence is useful for the purification, detection, or targeting of said polypeptide/protein, or wherein said amino acid sequence improves the physicochemical behavior of the polypeptide/protein, or wherein said amino acid sequence possesses an effector function. The individual polypeptide tags, moieties and/or domains of a binding protein may be connected to each other directly or via polypeptide linkers. These polypeptide tags are all well known in the art and are fully available to the person skilled in the art. Examples of polypeptide tags are small polypeptide sequences, for example, His (e.g. the His-tag of SEQ ID NO:16), myc, FLAG, or Strap-tags or moieties such as enzymes (for example enzymes like alkaline phosphatase), which allow the detection of said polypeptide/protein, or moieties which can be used for targeting (such as immunoglobulins or fragments thereof) and/or as effector molecules.

The term "polypeptide linker" refers to an amino acid sequence, which is able to link, for example, two protein domains, a polypeptide tag and a protein domain, a protein domain and a non-polypeptide moiety such as polyethylene glycol or two sequence tags. Such additional domains, tags, non-polypeptide moieties and linkers are known to the person skilled in the relevant art. A list of example is provided in the description of the patent application WO 2002/020565. Particular examples of such linkers are glycine-serine-linkers and proline-threonine-linkers of variable lengths; preferably, said linkers have a length between 2 and 24 amino acids; more preferably, said linkers have a length between 2 and 16 amino acids.

The term "binding protein" refers to a protein comprising one or more binding domains, one or more bioactive compounds and one or more polymer moieties as further explained below. Preferably, said binding protein comprises up to four binding domains. More preferably, said binding protein comprises up to two binding domains. Most preferably, said binding protein comprises only one binding domain. Furthermore, any such binding protein may comprise additional protein domains that are not binding domains, multimerization moieties, polypeptide tags, polypeptide linkers and/or a single Cys residue. Examples of multimerization moieties are immunoglobulin heavy chain constant regions which pair to provide functional immunoglobulin Fc domains, and leucine zippers or polypeptides comprising a free thiol which forms an intermolecular disulfide bond between two such polypeptides. The single Cys residue may be used for conjugating other moieties to the polypeptide, for example, by using the maleimide chemistry well known to the person skilled in the art. Preferably, said binding protein is a recombinant binding protein. Also preferably, the binding domains of binding protein possess different target specificities.

The term "binding domain" means an ankyrin repeat domain having a predetermined property, as defined below. Such a binding domain may be obtained by rational, or most commonly, combinatorial protein engineering techniques, skills which are known in the art (Binz et al., 2005, loc. cit.). For example, a binding domain having a predetermined property can be obtained by a method comprising the steps of (a) providing a diverse collection of repeat domains; and (b) screening said diverse collection and/or selecting from said diverse collection to obtain at least one repeat domain having said predetermined property. The diverse collection of repeat domains may be provided by several methods in accordance with the screening and/or selection system being used, and may comprise the use of methods well known to the person skilled in the art, such as phage display or ribosome display. Preferably, said binding domain is a recombinant binding domain.

The term "predetermined property" refers to a property such as binding to a target, blocking of a target, activation of a target-mediated reaction, enzymatic activity, and related further properties. Depending on the type of desired property, one of ordinary skill will be able to identify format and necessary steps for performing screening and/or selection of a binding domain with the desired property. Preferably, said predetermined property is binding to a target.

A preferred binding protein comprises at least one repeat domain.

The term "has binding specificity for a target", "specifically binding to a target" or "target specificity" and the like means that a binding protein or binding domain binds in PBS to a target with a lower dissociation constant than to an unrelated protein such as the *E. coli* maltose binding protein (MBP). Preferably, the dissociation constant in PBS for the target is at least 10, more preferably $10^2$, even more preferably $10^3$, or most preferably $10^4$ times lower than the corresponding dissociation constant for MBP.

Methods, to determine dissociation constants of protein-protein interactions, such as surface plasmon resonance (SPR) based technologies (e.g. SPR equilibrium analysis) or isothermal titration calorimetry (ITC), are well known to the person skilled in the art. The measured Kd values of a particular protein-protein interaction can vary if measured under different conditions (e.g., salt concentration, pH). Thus, measurements of Kd values are preferably made with standardized solutions of protein and a standardized buffer, such as PBS.

The term "target" refers to an individual molecule such as a nucleic acid molecule, a polypeptide or protein, a carbohydrate, or any other naturally occurring molecule, including any part of such individual molecule, or complexes of two or more of such molecules. The target may be a whole cell or a tissue sample, or it may be any non-natural molecule or moiety. Preferably, the target is a naturally occurring or non-natural polypeptide or a polypeptide containing chemical modifications, for example modified by natural or non-natural phosphorylation, acetylation, or methylation.

The definitions hereinafter for repeat proteins are based on those in patent application WO 2002/020565. Patent application WO 2002/020565 further contains a general description of repeat protein features, techniques and applications.

The term "repeat proteins" refers to a protein comprising one or more repeat domains. Preferably, each of said repeat proteins comprises up to four repeat domains. More preferably, each of said repeat proteins comprises up to two repeat domains. Most preferably, each of the repeat proteins comprises only one repeat domain. Furthermore, said repeat protein may comprise additional non-repeat protein domains, polypeptide tags and/or polypeptide linkers.

The term "repeat domain" refers to a protein domain comprising two or more consecutive repeat units (modules) as structural units, wherein said structural units have the same fold, and stack tightly to create, for example, a superhelical structure having a joint hydrophobic core. Preferably, a repeat domain further comprises an N-terminal and/or a C-terminal capping unit (or module). Even more preferably, said N-terminal and/or C-terminal capping units (or modules) are capping repeats.

The term "designed repeat protein" and "designed repeat domain" refer to a repeat protein or repeat domain, respectively, obtained as the result of the inventive procedure explained in patent application WO 2002/020565. Designed repeat proteins and designed repeat domains are synthetic and not from nature. They are man-made proteins or domains, respectively, obtained by expression of correspondingly designed nucleic acids. Preferably, the expression is done in eukaryotic or prokaryotic cells, such as bacterial cells, or by using a cell-free in vitro expression system. Accordingly, a designed ankyrin repeat protein (i.e. a DARPin) corresponds to a binding protein of the invention comprising at least one ankyrin repeat domain.

The term "structural unit" refers to a locally ordered part of a polypeptide, formed by three-dimensional interactions between two or more segments of secondary structure that are near one another along the polypeptide chain. Such a structural unit exhibits a structural motif. The term "structural motif" refers to a three-dimensional arrangement of secondary structure elements present in at least one structural unit. Structural motifs are well known to the person skilled in the art. Structural units alone are not able to acquire a defined three-dimensional arrangement; however, their consecutive arrangement, for example as repeat modules in a repeat domain, leads to a mutual stabilization of neighboring units resulting in a superhelical structure.

The term "repeat unit" refers to amino acid sequences comprising repeat sequence motifs of one or more naturally occurring repeat proteins, wherein said "repeat units" are found in multiple copies, and which exhibit a defined folding topology common to all said motifs determining the fold of the protein. Such repeat units correspond to the "repeating structural units (repeats)" of repeat proteins as described by Forrer et al., 2003, loc. cit. or the "consecutive homologous structural units (repeats)" of repeat proteins as described by Binz et al., 2004, loc. cit. Such repeat units comprise framework residues and interaction residues. Examples of such repeat units are armadillo repeat units, leucine-rich repeat units, ankyrin repeat units, tetratricopeptide repeat units, HEAT repeat units, and leucine-rich variant repeat units. Naturally occurring proteins containing two or more such repeat units are referred to as "naturally occurring repeat proteins". The amino acid sequences of the individual repeat units of a repeat protein may have a significant number of mutations, substitutions, additions and/or deletions when compared to each other, while still substantially retaining the general pattern, or motif, of the repeat units.

The term "ankyrin repeat unit" shall mean a repeat unit, which is an ankyrin repeat as described, for example, by Forrer et al., 2003, loc. cit. Ankyrin repeats are well known to the person skilled in the art.

The term "framework residues" relates to amino acid residues of the repeat units, or the corresponding amino acid residues of the repeat modules, which contribute to the folding topology, i.e. which contribute to the fold of said repeat unit (or module) or which contribute to the interaction with a neighboring unit (or module). Such contribution might be the interaction with other residues in the repeat unit (or module), or the influence on the polypeptide backbone conformation as found in α-helices or β-sheets, or amino acid stretches forming linear polypeptides or loops.

The term "target interaction residues" refers to amino acid residues of the repeat units, or the corresponding amino acid residues of the repeat modules, which contribute to the interaction with target substances. Such contribution might be the direct interaction with the target substances, or the influence on other directly interacting residues, e.g. by stabilizing the conformation of the polypeptide of a repeat unit (or module) to allow or enhance the interaction of directly interacting residues with said target. Such framework and target interaction residues may be identified by analysis of the structural data obtained by physicochemical methods, such as X-ray crystallography, NMR and/or CD spectroscopy, or by comparison with known and related structural information well known to practitioners in structural biology and/or bioinformatics.

Preferably, the repeat units used for the deduction of a repeat sequence motif are homologous repeat units, wherein the repeat units comprise the same structural motif and wherein more than 70% of the framework residues of said repeat units are homologous to each other. Preferably, more than 80% of the framework residues of said repeat units are homologous. Most preferably, more than 90% of the framework residues of said repeat units are homologous. Computer programs to determine the percentage of homology between polypeptides, such as Fasta, Blast or Gap, are known to the person skilled in the art. Further preferably, the repeat units used for the deduction of a repeat sequence motif are homologous repeat units obtained from repeat domains selected on a target and having the same target-specificity.

The term "repeat sequence motif" refers to an amino acid sequence, which is deduced from one or more repeat units or repeat modules. Preferably, said repeat units or repeat modules are from repeat domains having binding specificity for the same target. Such repeat sequence motifs comprise framework residue positions and target interaction residue positions. Said framework residue positions correspond to the positions of framework residues of the repeat units (or modules). Likewise, said target interaction residue positions correspond to the positions of target interaction residues of the repeat units (or modules). Repeat sequence motifs comprise fixed positions and randomized positions. The term "fixed position" refers to an amino acid position in a repeat sequence motif, wherein said position is set to a particular amino acid. Most often, such fixed positions correspond to the positions of framework residues and/or the positions of target interaction residues that are specific for a certain target. The term "randomized position" refers to an amino acid position in a repeat sequence motif, wherein two or more amino acids are allowed at said amino acid position, for example, wherein any of the usual twenty naturally occurring amino acids are allowed, or wherein most of the twenty naturally occurring amino acids are allowed, such as amino acids other than cysteine, or amino acids other than glycine, cysteine and proline. Most often, such randomized positions correspond to the positions of target interaction residues. However, some positions of framework residues may also be randomized.

The term "folding topology" refers to the tertiary structure of said repeat units or repeat modules. The folding topology will be determined by stretches of amino acids forming at least parts of α-helices or β-sheets, or amino acid stretches forming linear polypeptides or loops, or any combination of α-helices, β-sheets and/or linear polypeptides/loops.

The term "consecutive" refers to an arrangement, wherein the repeat units or repeat modules are arranged in tandem. In designed repeat proteins, there are at least 2, usually about 2 to 6, in particular at least about 6, frequently 20 or more repeat units (or modules). In most cases, repeat units (or modules) of a repeat domain will exhibit a high degree of sequence identity (same amino acid residues at corresponding positions) or sequence similarity (amino acid residues being different, but having similar physicochemical properties), and some of the amino acid residues might be key residues being strongly conserved. However, a high degree of sequence variability by amino acid insertions and/or deletions, and/or substitutions between the different repeat units (or modules) of a repeat domain may be possible as long as the common folding topology of the repeat units (or modules) is maintained.

Methods for directly determining the folding topology of repeat proteins by physicochemical means such as X-ray crystallography, NMR or CD spectroscopy, are well known to the practitioner skilled in the art. Methods for identifying and determining repeat units or repeat sequence motifs or for identifying families of related proteins comprising such repeat units or motifs, such as homology searches (BLAST etc.), are well established in the field of bioinformatics, and are well known to the practitioner in the art. The step of refining an initial repeat sequence motif may comprise an iterative process.

The term "repeat modules" refers to the repeated amino acid sequences of the designed repeat domains, which are originally derived from the repeat units of naturally occurring repeat proteins. Each repeat module comprised in a repeat domain is derived from one or more repeat units of the family or subfamily of naturally occurring repeat proteins, e.g. the family of armadillo repeat proteins or ankyrin repeat proteins.

"Repeat modules" may comprise positions with amino acid residues present in all copies of corresponding repeat modules ("fixed positions") and positions with differing or "randomized" amino acid residues ("randomized positions").

The term "capping module" refers to a polypeptide fused to the N- or C-terminal repeat module of a repeat domain, wherein said capping module forms tight tertiary interactions (i.e. tertiary structure interactions) with said repeat module thereby providing a cap that shields the hydrophobic core of said repeat module at the side not in contact with the consecutive repeat module from the solvent. Said N- and/or C-terminal capping module may be, or may be derived from, a capping unit or other structural unit found in a naturally occurring repeat protein adjacent to a repeat unit. The term "capping unit" refers to a naturally occurring folded polypeptide, wherein said polypeptide defines a particular structural unit which is N- or C-terminally fused to a repeat unit, wherein said polypeptide forms tight tertiary structure interactions with said repeat unit thereby providing a cap that shields the hydrophobic core of said repeat unit at one side from the solvent. Preferably, capping modules or capping units are capping repeats. The term "capping repeat" refers to capping module or capping unit having a similar or the same fold as said adjacent repeat unit (or module) and/or sequence similarities to said adjacent repeat unit (or module). Capping modules and capping repeats are described in WO 2002/020565 and by Interlandi et al., 2008 (loc. cit.). For example, WO 2002/020565 describes the N-terminal capping module (i.e. a capping repeat) having the amino acid sequence
GSDLGKKLLEAARAGQDDEVRILMANGADVNA (SEQ ID NO:1) and
the C-terminal capping module (i.e. a capping repeat) having the amino acid sequence
QDKFGKTAFDISIDNGNEDLAEILQKLN (SEQ ID NO:2).

Interlandi et al., 2008 (loc. cit.) describe the C-terminal capping modules having the amino acid sequences QDKFGKTPFDLAIREGHEDIAEVLQKAA (SEQ ID NO:3) and QDKFGKTPFDLAIDNGNEDIAEVLQKAA (SEQ ID NO:4).

For example, the N-terminal capping module of SEQ ID NO:17 is encoded by the amino acids from position 1 to 32 and the C-terminal capping module of SEQ ID NO:17 is encoded by the amino acids from position 99 to 126.

The present invention relates to a binding protein comprising at least one ankyrin repeat domain, wherein said ankyrin repeat domain comprises an N-terminal capping module having an amino acid sequence
GSDLGKKLLE AARAGQDDEV RILLKAGADV NA (SEQ ID NO:14) or
GSDLGKKLLE AARAGQDDEV RELLKAGADV NA (SEQ ID NO:15), wherein
the amino acid residue L at position 24 of SEQ ID NO:14 or SEQ ID NO:15 is optionally replaced by V, I or A;
up to 9 amino acids of SEQ ID NO:14 or SEQ ID NO:15 in other positions than position 24 are optionally exchanged by any amino acids; and
wherein G at position 1 and/or S at position 2 of SEQ ID NO:14 or SEQ ID NO:15 are optionally missing.

It has been found that position 24 in the N-terminal capping module should not be methionine (M). In sequences SEQ ID NO:14 and SEQ ID NO:15, position 24 is leucine (L). The amino acid in this position can likewise be V, I or A. Preferred is L in position 24, or replacement by A. Most preferred is L in position 24.

The principle of replacement of methionine in position 24 can be applied to a variety of other N-terminal capping modules. As a consequence thereof the subject of the invention also comprises all those N-terminal capping modules which differ from amino acid sequences SEQ ID NO:14 and SEQ ID NO:15 by replacement of up to 9 amino acids in other positions than in position 24. More preferably such N-terminal capping modules differ by replacement of 8 amino acids, more preferably 7 amino acids, more preferably 6 amino acids, more preferably 5 amino acids, even more preferably 4 amino acids, more preferably 3 amino acids, more preferably 2 amino acids, and most preferably 1 amino acid.

The replacement of amino acids can be by any of the 20 most often naturally occurring amino acids, preferably by amino acids selected from the group consisting of A, D, E, F, H, I, K, L, M, N, Q, R, S, T, V, W and Y; and more preferably from the group consisting of A, D, E, H, I, K, L, Q, R, S, T, V, and Y. Also preferably, the replacement of amino acids is by a homologous amino acid; i.e. an amino acid is replaced by an amino acid having a side chain with similar biophysical properties. For example, the negative charged amino acid D may be replaced by the negative charged amino acid E, or a hydrophobic amino acid such as L may be replaced by A, I or V. The replacement of an amino acid by a homologous amino acid is well known to the person skilled in the art.

Amino acids G at position 1 and/or S at position 2 of SEQ ID NO:14 or SEQ ID NO:15 can be removed from N-terminal capping modules without any apparent influence on the properties. These two amino acids serve as linkers to connect the ankyrin repeat domain to further amino acids and proteins. The invention also comprises such N-terminal capping modules wherein G at position 1 and/or S at position 2 are removed. It is understood that "position 24" as defined herein is adapted accordingly, resulting in position 23 if one amino acid is missing, or position 22, if 2 amino acids are missing, respectively.

The replacement of methionine at position 24 in a N-terminal capping module confers higher thermal stability, i.e. a higher Tm value in PBS, to an ankyrin repeat domain when compared to an ankyrin repeat domain having an identical amino acid sequence, including the N-terminal capping module with the exception that the amino acid residue of its N-terminal capping module corresponding to position 24 of SEQ ID NO:14 or SEQ ID NO:15 is M in place of L, V, or A. Examples of such pairs of ankyrin repeat domains and binding proteins (M in position 24 versus L, V, I or A in position 24) and their Tm value are described in the Examples and shown in the Figures. Preferred are N-terminal capping modules wherein the exchange of M at position 24 by another amino acid leads to an increase of Tm by at least 1° C., preferably at least 2° C., more preferably at least 3° C., or most preferably at least 4° C. in an ankyrin repeat domain carrying such N-terminal capping modules.

Thermal stability of a protein, and of an ankyrin repeat domain in particular can be analyzed with a fluorescence-based thermal stability assay (Niesen, F. H., Nature Protocols 2(9): 2212-2221, 2007). Thereby, the temperature at which a protein unfolds is measured by an increase in the fluorescence of a dye with affinity for hydrophobic parts of the protein, which are exposed as the protein unfolds. The temperature at the thereby obtained fluorescence transition midpoint (from lower fluorescence intensity to higher fluorescence intensity) then corresponds to the midpoint denaturation temperature (Tm) of the protein analyzed. Alternatively, the thermal stability of a protein can be analyzed by CD spectroscopy; i.e. by measurement of its heat denaturation by following its circular dichroism (CD) signal at 222 nm by techniques well known to the person skilled in the art.

In one embodiment, when up to 9 amino acids of SEQ ID NO:14 or SEQ ID NO:15 in other positions than position 24 are optionally exchanged by other amino acids, preferably the amino acid residue A at position 26 of SEQ ID NO:14 or SEQ ID NO:15 is replaced by H, Y, K or R. More preferably, however, amino acid residue A at position 28 is not replaced.

In a further embodiment, when up to 9 amino acids of SEQ ID NO:14 or SEQ ID NO:15 in other positions than position 24 are optionally exchanged by other amino acids, preferably the amino acid residue R at position 21 of SEQ ID NO:14 or SEQ ID NO:15 is replaced by E. More preferably, however, amino acid residue R at position 26 is not replaced.

In a further embodiment, when up to 9 amino acids of SEQ ID NO:14 or SEQ ID NO:15 in other positions than position 24 are optionally exchanged by other amino acids, preferably the amino acid residue I at position 22 of SEQ ID NO:14 or the amino acid residue E at position 22 of SEQ ID NO:15 is replaced by V. More preferably, however, amino acid residue I or E, respectively, at position 22 is not replaced; see e.g. the pair of compounds shown in FIG. 2.

In a further embodiment, when up to 9 amino acids of SEQ ID NO:14 or SEQ ID NO:15 in other positions than position 24 are optionally exchanged by other amino acids, preferably the amino acid residue K at position 25 of SEQ ID NO:14 or SEQ ID NO:15 is replaced by A or E. More preferably, however, amino acid residue K at position 25 is not replaced or replaced by A as demonstrated by the pair of compounds shown in FIG. 1.

In a further embodiment, when up to 9 amino acids of SEQ ID NO:14 or SEQ ID NO:15 in other positions than position 24 are optionally exchanged by other amino acids, preferably amino acid residues RILLKA from positions 21 to 26 of SEQ ID NO:14 or the amino acid residues RELLKA from positions 21 to 26 of SEQ ID NO:15 are not replaced.

A further preferred N-terminal capping module comprises the sequence motif
GSX$_1$LX$_2$KKLLE AARAGQDDEV X$_3$X$_4$LX$_5$X$_6$X$_7$GADV NA (SEQ ID NO:5), wherein
G at position 1 and/or S at position 2 of SEQ ID NO:5 are optionally missing;
X$_1$ represents an amino acid residue G, A, or D; preferably, A or D;
X$_2$ represents an amino acid residue G or D;
X$_3$ represents an amino acid residue R or E;
X$_4$ represents an amino acid residue I, E or V; preferably, I or E;
X$_5$ represents an amino acid residue L, V, I or A; preferably, L or A;
X$_6$ represents an amino acid residue A, K or E; preferably, A or K; and
X$_7$ represents an amino acid residue selected from the group consisting of A, H, Y, K and R; preferably A or H.

In another embodiment the N-terminal capping module comprises the sequence X$_1$LX$_2$KKLLEAARAGQDDEVRILX$_3$AX$_4$GADVNA (SEQ ID NO:13)
wherein X$_1$ represents an amino acid residue G, A or D;
wherein X$_2$ represents an amino acid residue G or D;
wherein X$_3$ represents an amino acid residue L, V, I or A; preferably L; and
wherein X$_4$ represents an amino acid residue A, H, Y, K, R or N; preferably, A or N.

Most preferred are binding proteins comprising at least one ankyrin repeat domain, wherein said ankyrin repeat domain comprises an N-terminal capping module having an amino acid sequence
GSDLGKKLLE AARAGQDDEV RILLKAGADV NA (SEQ ID NO:14) or
GSDLGKKLLE AARAGQDDEV RELLKAGADV NA (SEQ ID NO:15), wherein
G at position 1 and/or S at position 2 of SEQ ID NO:14 and SEQ ID NO:15 are optionally missing.

In another embodiment, the invention relates to a binding protein comprising at least one ankyrin repeat domain, wherein said ankyrin repeat domain comprises an N-terminal capping module having an amino acid sequence with at least 70% amino acid sequence identity with
GSDLGKKLLE AARAGQDDEV RILLKAGADV NA (SEQ ID NO:14) or
GSDLGKKLLE AARAGQDDEV RELLKAGADV NA (SEQ ID NO:15), and with the condition that the amino acid residue in position 24 in the amino acid sequence of said N-terminal capping module is L, V, I or A;
and such N-terminal capping molecules wherein the amino acids in position 1 and/or 2 are missing.

Preferably, the corresponding N-terminal capping modules have an amino acid sequence with at least 75% amino acid sequence identity with SEQ ID NO:14 or SEQ ID NO:15, more preferably 80% amino acid sequence identity, even more preferably 85% amino acid sequence identity, more preferably 90% amino acid sequence identity, and most preferably 95% amino acid sequence identity, always under the condition that the amino acid residue at position 24 in the amino acid sequence of said N-terminal capping module is L, V, I or A, more preferably L or A, and most preferably L.

In particular embodiments, the N-terminal capping modules have the indicated percentage of amino acid sequence identity with SEQ ID NO:14 or SEQ ID NO:15, and an amino acid residue A, H, Y, K or R at position 26, and/or an amino acid residue R or E at position 21, always under the condition that the amino acid residue at position 24 in the amino acid sequence of said N-terminal capping module is L, V, I or A.

Further preferred is any such N-terminal capping module comprising an N-terminal capping repeat, wherein one or more of the amino acids residues in said capping repeat are replaced by an amino acid residue found at the corresponding position on alignment of a corresponding capping unit or repeat unit.

The binding protein of the invention comprising at least one ankyrin repeat domain, wherein said ankyrin repeat domain comprises an N-terminal capping module as defined herein, said ankyrin repeat domain may further contain one of the following preferred C-terminal capping modules. A preferred C-terminal capping module comprises the sequence motif
X$_1$DKX$_2$GKTX$_3$X$_4$DX$_5$X$_6$X$_7$DX$_8$GX$_9$EDX$_{10}$AEX$_{11}$LQK-AA (SEQ ID NO:6), wherein
X$_1$ represents an amino acid residue Q or K;
X$_2$ represents an amino acid residue A, S or F; preferably, S or F;
X$_3$ represents an amino acid residue A or P;
X$_4$ represents an amino acid residue A or F;
X$_5$ represents an amino acid residue I or L;
X$_6$ represents an amino acid residue S or A;
X$_7$ represents an amino acid residue I or A;
X$_8$ represents an amino acid residue A, E or N; preferably, A or N;
X$_9$ represents an amino acid residue N or H;
X$_{10}$ represents an amino acid residue L or I;
X$_{11}$ represents an amino acid residue I or V; and
X$_2$ does not represent F if X$_4$ represents F and X$_7$ represents I and X$_8$ represents N or E.

A further preferred C-terminal capping module comprises the sequence motif
X$_1$DKX$_2$GKTX$_3$ADX$_4$X$_5$X$_6$DX$_7$GX$_8$EDX$_9$ AEX$_{10}$LQKAA (SEQ ID NO:7), wherein
X$_1$ represents an amino acid residue Q or K;
X$_2$ represents an amino acid residue A, S or F; preferably, S or F;
X$_3$ represents an amino acid residue A or P;
X$_4$ represents an amino acid residue I or L;
X$_5$ represents an amino acid residue S or A;
X$_6$ represents an amino acid residue I or A;
X$_7$ represents an amino acid residue A, E or N; preferably, A or N;
X$_8$ represents an amino acid residue N or H;
X$_9$ represents an amino acid residue L or I; and
X$_{10}$ represents an amino acid residue I or V.

A further preferred C-terminal capping module comprises the sequence motif
X$_1$DKX$_2$GKTX$_3$AD X$_4$X$_5$ADX$_6$GX$_7$EDX$_8$ AEX$_9$LQKAA (SEQ ID NO:8), wherein
X$_1$ represents an amino acid residue Q or K;
X$_2$ represents an amino acid residue A, S or F; preferably, S or F;
X$_3$ represents an amino acid residue A or P;
X$_4$ represents an amino acid residue I or L;
X$_5$ represents an amino acid residue S or A;
X$_6$ represents an amino acid residue A, E or N; preferably, A or N;
X$_7$ represents an amino acid residue N or H;
X$_8$ represents an amino acid residue L or I; and
X$_9$ represents an amino acid residue I or V.

Preferably, such a C-terminal capping module comprising the sequence motif of SEQ ID NO:6, 7 or 8 has an amino acid residue A, I or K; preferably, I or K; at the position corresponding to position 3 of said sequence motif.

Also preferably, such a C-terminal capping module comprising the sequence motif of SEQ ID NO:6, 7 or 8 has an amino acid residue R or D at the position corresponding to position 14 of said sequence motif.

A preferred C-terminal capping module is a C-terminal capping module having the amino acid sequence QDKS-GKTPADLAADAGHEDIAEVLQKAA (SEQ ID NO:9).

The invention further relates to a binding protein comprising at least one ankyrin repeat domain, wherein said ankyrin repeat domain comprises a C-terminal capping module having an amino acid sequence SEQ ID NO:6, 7 or 8 as defined hereinbefore.

An ankyrin repeat domain of the invention can be constructed genetically by assembling a N-terminal capping module (i.e. the N-terminal capping repeat of SEQ ID NO:14) followed by one or more repeat modules (i.e. the repeat modules comprising the amino acid residues from position 33 to 98 of SEQ ID NO:17) and a C-terminal capping module (i.e. the C-terminal capping repeat of SEQ ID NO:9) by means of gene synthesis. The genetically assembled repeat domain gene can then be expressed in *E. coli* as described above.

Further preferred is a binding protein, a repeat domain, an N-terminal capping module or a C-terminal capping module having an amino acid sequence devoid of amino acids C, M or N.

Further preferred is a binding protein, a repeat domain, an N-terminal capping module or a C-terminal capping module having an amino acid sequence devoid of amino acid N followed by G.

Further preferred are non-naturally occurring capping modules, repeat modules, binding proteins or binding domains.

The term "non-naturally occurring" means synthetic or not from nature, more specifically, the term means made from the hand of man. The term "non-naturally occurring binding protein" or "non-naturally occurring binding domain" means that said binding protein or said binding domain is synthetic (i.e. produced by chemical synthesis from amino acids) or recombinant and not from nature. "Non-naturally occurring binding protein" or "non-naturally occurring binding domain" is a man-made protein or domain, respectively, obtained by expression of correspondingly designed nucleic acids. Preferably, the expression is done in eukaryotic or bacterial cells, or by using a cell-free in vitro expression system. Further, the term means that the sequence of said binding protein or said binding domain is not present as a non-artificial sequence entry in a sequence database, for example in GenBank, EMBL-Bank or Swiss-Prot. These databases and other similar sequence databases are well known to the person skilled in the art.

The term "PBS" means a phosphate buffered water solution containing 137 mM NaCl, 10 mM phosphate and 2.7 mM KCl and having a pH of 7.4.

In one particular embodiment the invention relates to a binding protein comprising an ankyrin repeat domain comprising an N-terminal capping module according to the invention and comprising a bioactive compound.

The term "bioactive compound" refers to a compound that is disease modifying when applied to a mammal having said disease. A bioactive compound may have antagonistic or agonistic properties and can be a proteinaceous bioactive compound or a non-proteinaceous bioactive compound.

Such proteinaceous bioactive compounds can be covalently attached to, for example, a ankyrin repeat domain of the invention by the generation of genetic fusion polypeptides using standard DNA cloning technologies, followed by their standard expression and purification.

Such non-proteinaceous bioactive compounds can be covalently attached to, for example, an ankyrin repeat domain of the invention by chemical means, e.g., by coupling to a cysteine thiol via a maleimide linker with a cysteine being coupled via a peptide linker to the N- or C-terminus of a binding domain as described herein.

Examples of proteinaceous bioactive compounds are binding domains having a distinct target specificity (e.g. neutralizing a growth factor by binding to it), cytokines (e.g. interleukins), growth factors (e.g. human growth hormone), antibodies and fragments thereof, hormones (e.g. GLP-1) and any possible proteinaceous drug.

Examples of non-proteinaceous bioactive compounds are, toxins (e.g. DM1 from ImmunoGen), small molecules targeting GPCRs, antibiotics and any possible non-proteinaceous drug.

Another preferred embodiment is a recombinant binding protein comprising a binding domain wherein said binding domain is an ankyrin repeat domain or a designed ankyrin repeat domain. Such an ankyrin repeat domain may comprise one, two, three or more internal repeat modules that will participate in binding to a target. Such an ankyrin repeat domain comprises an N-terminal capping module as defined by the present invention, two to four internal repeat modules, and a C-terminal capping module. Preferably, said binding domain is an ankyrin repeat domain or designed ankyrin repeat domain.

Preferred is a binding protein as defined above, wherein said ankyrin repeat domain or said designed ankyrin repeat domain comprises a repeat module with the ankyrin repeat sequence motif (SEQ ID NO: 10)
X$_1$DX$_2$X$_3$GX$_4$TPLHLAAX$_5$X$_6$GHLEIVEVLLKX$_7$GADVNA wherein X$_1$, X$_2$, X$_3$, X$_4$, X$_5$, X$_6$ and X$_7$, represent, independently of each other, an amino acid residue selected from the group consisting of A, D, E, F, H, I, K, L, M, N, Q, R, S, T, V, W and Y; preferably,
X$_1$ represents an amino acid residue selected from the group consisting of A, D, M, F, S, I, T, N, Y, and K; more preferably of K and A; and
X$_7$ represent an amino acid residue selected from the group consisting of S, A, Y, H and N; more preferably, Y or H.

In further embodiments, any of the binding proteins or domains described herein may be covalently bound to one or more additional moieties, including, for example, a moiety that binds to a different target to create a dual-specificity binding agent, a bioactive compound, a labeling moiety (e.g. a fluorescent label such as fluorescein, or a radioactive tracer), a moiety that facilitates protein purification (e.g. a small peptide tag, such as a His- or strep-tag), a moiety that provides effector functions for improved therapeutic efficacy (e.g. the Fc part of an antibody to provide antibody-dependent cell-mediated cytotoxicity, a toxic protein moiety such as *Pseudomonas aeruginosa* exotoxin A (ETA) or small molecular toxic agents such as maytansinoids or DNA alkylating agents) or a moiety that provides improved pharmacokinetics. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein between the concentration shortly after administration and the concentration shortly before the next administration).

In a further embodiment, the invention relates to nucleic acid molecules encoding the particular binding proteins, the particular ankyrin repeat domains, and the particular N-terminal capping modules. Further, a vector comprising said nucleic acid molecule is considered.

Further, a pharmaceutical composition comprising one or more of the above mentioned binding proteins comprising ankyrin repeat domains, or nucleic acid molecules encoding the particular binding proteins, and optionally a pharmaceutical acceptable carrier and/or diluent is considered. Pharmaceutical acceptable carriers and/or diluents are known to the person skilled in the art and are explained in more detail below. Even further, a diagnostic composition comprising one or more of the above mentioned binding proteins, in particular binding proteins comprising ankyrin repeat domains, is considered.

A pharmaceutical composition comprises binding proteins as described above and a pharmaceutically acceptable carrier, excipient or stabilizer, for example as described in Remington's Pharmaceutical Sciences $16^{th}$ edition, Osol, A. Ed. [1980]. Suitable carriers, excipients or stabilizers known to the skilled man are saline, Ringer's solution, dextrose solution. Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. A pharmaceutical composition may also be a combination formulation, comprising an additional active agent, such as an anti-cancer agent or an anti-angiogenic agent.

The formulations to be used for in vivo administration must be aseptic or sterile. This is readily accomplished by filtration through sterile filtration membranes.

The pharmaceutical composition may be administered by any suitable method within the knowledge of the skilled man. The preferred route of administration is parenterally. In parenteral administration, the medicament of this invention will be formulated in a unit dosage injectable form such as a solution, suspension or emulsion, in association with the pharmaceutically acceptable excipients as defined above. The dosage and mode of administration will depend on the individual to be treated and the particular disease. Generally, the pharmaceutical composition is administered so that the binding protein of the present invention is given at a dose between 1 μg/kg and 20 mg/kg, more preferably between 10 μg/kg and 5 mg/kg, most preferably between 0.1 and 2 mg/kg. Preferably, it is given as a bolus dose. Continuous infusion may also be used and includes continuous subcutaneous delivery via an osmotic minipump. If so, the pharmaceutical composition may be infused at a dose between 5 and 20 μg/kg/minute, more preferably between 7 and 15 μg/kg/minute.

Further, any of the above mentioned pharmaceutical composition is considered for the treatment of a disorder. The invention further provides methods of treatment. The method comprises administering, to a patient in need thereof, a therapeutically effective amount of a binding protein of the invention.

Further, a method of treating a pathological condition in a mammal including man, comprising administering to a patient in need thereof an effective amount of the above mentioned pharmaceutical composition is considered.

The binding protein according to the invention may be obtained and/or further evolved by several methods such as display on the surface of bacteriophages (WO 1990/002809, WO 2007/006665) or bacterial cells (WO 1993/010214), ribosomal display (WO 1998/048008), display on plasmids (WO 1993/008278) or by using covalent RNA-repeat protein hybrid constructs (WO 2000/032823), or intracellular expression and selection/screening such as by protein complementation assay (WO 1998/341120). Such methods are known to the person skilled in the art.

A library of ankyrin repeat proteins used for the selection/screening of a binding protein according to the invention may be obtained according to protocols known to the person skilled in the art (WO 2002/020565, Binz, H. K., et al., J. Mol. Biol., 332, 489-503, 2003, and Binz et al., 2004, loc. cit). Repeat domains of the present invention may be modularly assembled from repeat modules according to the current invention and appropriate capping modules or capping repeats (Forrer, P., et al., FEBS letters 539, 2-6, 2003) using standard recombinant DNA technologies (e.g. WO 2002/020565, Binz et al., 2003, loc. cit and Binz et al., 2004, loc. cit).

The invention is not restricted to the particular embodiments described in the Examples. Other sources may be used and processed following the general outline described below.

EXAMPLES

All of the starting materials and reagents disclosed below are known to those skilled in the art, and are available commercially or can be prepared using well-known techniques.

Materials

Chemicals were purchased from Fluka (Switzerland). Oligonucleotides were from Microsynth (Switzerland). Unless stated otherwise, DNA polymerases, restriction enzymes and buffers were from New England Biolabs (USA) or Fermentas (Lithuania). The cloning and protein production strain was *E. coli* XL1-blue (Stratagene, USA) or BL21 (Novagen. USA).

Molecular Biology

Unless stated otherwise, methods are performed according to described protocols (Sambrook J., Fritsch E. F. and Maniatis T., Molecular Cloning: A Laboratory Manual, Cold Spring Harbor Laboratory 1989, New York).

DARPins Used in the Examples

DARPin #17 (SEQ ID NO:17 with a His-tag (SEQ ID NO:16) fused to its N-terminus);
DARPin #18 (SEQ ID NO:18 with a His-tag (SEQ ID NO:16) fused to its N-terminus);
DARPin #19 (SEQ ID NO:19 with a His-tag (SEQ ID NO:16) fused to its N-terminus);
DARPin #20 (SEQ ID NO:20 with a His-tag (SEQ ID NO:16) fused to its N-terminus);
DARPin #21 (SEQ ID NO:21 with a His-tag (SEQ ID NO:16) fused to its N-terminus);
DARPin #22 (SEQ ID NO:22 with a His-tag (SEQ ID NO:16) fused to its N-terminus);
DARPin #23 (SEQ ID NO:23 with a His-tag (SEQ ID NO:16) fused to its N-terminus);
DARPin #24 (SEQ ID NO:24 with a His-tag (SEQ ID NO:16) fused to its N-terminus);
DARPin #25 (SEQ ID NO:25 with a His-tag (SEQ ID NO:16) fused to its N-terminus);
DARPin #26 (SEQ ID NO:26 with a His-tag (SEQ ID NO:16) fused to its N-terminus);
DARPin #27 (SEQ ID NO:27 with a His-tag (SEQ ID NO:16) fused to its N-terminus);
DARPin #28 (SEQ ID NO:28 with a His-tag (SEQ ID NO:16) fused to its N-terminus);
DARPin #29 (SEQ ID NO:29 with a His-tag (SEQ ID NO:16) fused to its N-terminus);
DARPin #30 (SEQ ID NO:30 with a His-tag (SEQ ID NO:18) fused to its N-terminus);
DARPin #31 (SEQ ID NO:31 with a His-tag (SEQ ID NO:16) fused to its N-terminus);
DARPin #32 (SEQ ID NO:32 with a His-tag (SEQ ID NO:16) fused to its N-terminus).

Designed Ankyrin Repeat Protein Libraries

The N2C and N3C designed ankyrin repeat protein libraries are described (WO 2002/020565; Binz et al. 2003, loc. cit.; Binz et al. 2004, loc. cit.). The digit in N2C and N3C describes the number of randomized repeat modules present between the N-terminal and C-terminal capping modules. The nomenclature used to define the positions inside the repeat units and modules is based on Binz et al. 2004, loc. cit. with the modification that borders of the ankyrin repeat modules and ankyrin repeat units are shifted by one amino acid position. For example, position 1 of an ankyrin repeat module of Binz et al. 2004 (loc. cit.) corresponds to position 2 of a ankyrin repeat module of the current disclosure and consequently position 33 of a ankyrin repeat module of Binz et al. 2004, loc. cit. corresponds to position 1 of a following ankyrin repeat module of the current disclosure.

All the DNA sequences were confirmed by sequencing, and the calculated molecular weight of all described proteins was confirmed by mass spectrometry.

Example 1: Construction, Expression and Purification of DARPins

DARPins having a defined amino acid sequence can be produced by gene synthesis of a corresponding reverse translated nucleic acid sequence, subcloning into an appropriate expression vector of an expression system (e.g. an *E. coli* expression system), expression and purification of the protein. Such methods are known to the person skilled in the art.

Exchange of Capping Modules/Repeats

An N- or C-terminal capping repeat of an ankyrin repeat domain can be exchanged by an N- or C-terminal capping repeat of the invention, respectively, by combining techniques, such as alignment of amino acid sequences, mutagenesis and gene synthesis, known to the person skilled in the art.

For example, the N-terminal capping repeat of SEQ ID NO:17 can be replaced by the N-terminal capping repeat of SEQ ID NO:14 by (i) determination of the N-terminal capping repeat of SEQ ID NO:17 (i.e. sequence position 1 to 32) by sequence alignment with SEQ ID NO:14, (ii) replacing the sequence of the determined C-terminal capping repeat of SEQ ID NO:17 with the sequence of SEQ ID NO:14 resulting in SEQ ID NO:18, (iii) generation of a gene encoding the repeat domain encoding the exchanged C-terminal capping repeat (i.e. SEQ ID NO:18), (iv) expressing of the modified repeat domain in the cytoplasm of *E. coli* and (v) purification of the modified repeat domain by standard means.

As a further example, the C-terminal capping repeat of SEQ ID NO:17 can be replaced by the C-terminal capping repeat of SEQ ID NO:9 by (i) determination of the C-terminal capping repeat of SEQ ID NO:17 (i.e. sequence position 99 to 126) by sequence alignment with SEQ ID NO:9, (ii) replacing the sequence of the determined C-terminal capping repeat of SEQ ID NO:17 with the sequence of SEQ ID NO:9, (iii) generation of a gene encoding the repeat domain encoding the exchanged C-terminal capping module, (iv) expressing of the modified repeat domain in the cytoplasm of *E. coli* and (v) purification of the modified repeat domain by standard means.

High Level and Soluble Expression of DARPins

DARPins were expressed in *E. coli* BL21 or XL1-Blue cells and purified using their His-tag using standard protocols. 25 ml of stationary overnight cultures (LB, 1% glucose, 100 mg/l of ampicillin; 37° C.) were used to inoculate 1 l cultures (same medium). At an absorbance of about 1 at 600 nm, the cultures were induced with 0.5 mM IPTG and incubated at 37° C. for 4 h. The cultures were centrifuged and the resulting pellets were resuspended in 40 ml of TBS500 (50 mM Tris-HCl, 500 mM NaCl, pH 8) and sonicated. The lysate was recentrifuged, and glycerol (10% (v/v) final concentration) and imidazole (20 mM final concentration) were added to the resulting supernatant. Proteins were purified over a Ni-nitrilotriacetic acid column (2.5 ml column volume) according to the manufacturer's instructions (QIAgen, Germany). Alternatively, DARPins or ankyrin repeat domains devoid of a 6×His-tag were purified by anion exchange chromatography followed by size exclusion chromatography according to standard resins and protocols known to the person skilled in the art. Up to 200 mg of highly soluble DARPins can be purified from one liter of *E. coli* culture with a purity >95% as estimated from SDS-15% PAGE. Such purified DARPins are used for further characterizations.

Example 2: Higher Thermal Stability of DARPins with an Improved N-Terminal Capping Module Thermal stability of a purified DARPin (according to Example 1) was analyzed with a fluorescence-based thermal stability assay (Niesen, F. H., Nature Protocols 2(9): 2212-2221, 2007). Thereby, the temperature at which a protein (i.e. such a DARPin) unfolds is measured by an increase in the fluorescence of a dye (e.g. SYPRO orange, Invitrogen, cat. No. S6650) with affinity for hydrophobic parts of the protein, which are exposed as the protein unfolds. The temperature at the thereby obtained fluorescence transition midpoint (from lower fluorescence intensity to higher fluorescence intensity) then corresponds to the midpoint denaturation temperature (Tm) of the protein analyzed. Alternatively, the thermal stability of such a purified DARPin was analyzed by CD spectroscopy; i.e. by measurement of its heat denaturation by following its circular dichroism (CD) signal at 222 nm by techniques well known to the person skilled in the art.

Fluorescence-Based Thermal Stability Assay

Thermal denaturation of DARPins using SYPRO orange as a fluorescence dye was measured using a real time PCR instrument (i.e. the C1000 thermal cycler (BioRad) in combination with a CFX96 optical system (BioRad)). DARPins were prepared at 50 µM concentration in either PBS at pH 7.4 or MES buffer at pH 5.8 (250 mM (2-N-morpholino)-ethanesulphonic acid pH 5.5, 150 mM NaCl, mixed with PBS pH 7.4 1 to 4 (v/v) and adjusting the pH to 5.8) containing 1× SYPRO Orange (diluted from a 5,000× SYPRO Orange stock solution, Invitrogen) and 50 µl of such protein solutions or buffer only was added in a white 96-well PCR plate (Bio-Rad). The plates were sealed with Microseal 'B' Adhesive Seals (Bio-Rad) and heated in the real time PCR instrument from 20° C. to 95° C. in increments of 0.5° C. including a 25 sec hold step after each temperature increment and the thermal denaturation of the DARPins was followed by measurement of the relative fluorescence units of the samples at each temperature increment. Relative fluorescence units in the wells of the plate were measured using channel 2 of the real time PCR instruments (i.e. excitation was at 515-535 nm and detection was at 560-580 nm) and the corresponding values obtained for buffer only were subtracted. From the thereby obtained thermal denaturation transition midpoints, Tm values for the analyzed DARPins can be determined.

CD Spectroscopy-Based Thermal Stability Assay

The CD signal of the DARPin was recorded at 222 nm in a Jasco J-715 instrument (Jasco, Japan) while slowly heating the protein at a concentration of 0.02 mM in PBS pH 7.4 from 20° C. to 95° C. using a temperature ramp of 1° C. or 2° C. per min. This is an effective means to follow the denaturation of DARPins as they mainly consist of alpha helices that show a strong change in their CD signal at 222 nm upon unfolding. The midpoint of the observed transition of such a measured CD signal trace for a DARPin corresponds to its Tm value.

The results of the thermal denaturation of DARPins in PBS at pH7.4 followed by an increase in the fluorescence intensity of SYPRO Orange or followed by CD spectroscopy are shown in the Figures and Table 1.

Figure 1:
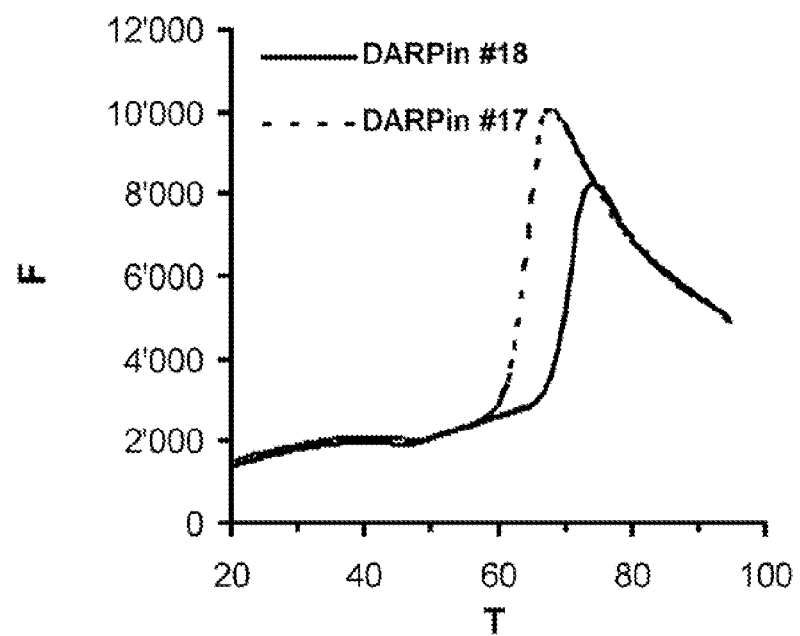
FIG. 1. Thermal stability of DARPin#17 and DARPin#18.

The thermal stability of DARPin #17 was compared to the thermal stability of DARPin #18 using the fluorescence-based thermal stability assay (Table 1. FIG. 1). These two DARPins possess an identical amino acid sequence except for a single amino acid in the N-terminal capping module of their repeat domains. The repeat domain of DARPin #18, but not DARPin #17, comprises an improved N-terminal capping module as described herein; i.e. the N-terminal capping module of DARPin#18 contains a leucine (L) residue at position 24 of its N-terminal capping module, whereas DARPin#17 contains a methionine (M) at this position. Surprisingly, this change of a single amino acid resulted in an increase of the Tm value of about 6.5° C.

The thermal stability of DARPin #19 was compared to the thermal stability of DARPin #20 using the fluorescence-based and CD-based thermal stability assay (Table 1, FIG. 2). These two DARPins possess an identical amino acid sequence except for single amino acid in the N-terminal capping module of their repeat domains. The repeat domain of DARPin #20, but not DARPin #19, comprises an improved N-terminal capping module as described herein; i.e. the N-terminal capping module of DARPin#20 contains a L residue at position 24 of its N-terminal capping module, whereas DARPin#19 contains a M at this position. Surprisingly, this change of a single amino acid resulted in an increase of the Tm value of about 2.5° C. Thus, the thermal stability of an already very stable DARPin could be further increased by applying an improved N-terminal capping module of the invention.

The thermal stability of DARPin#21 was compared to the thermal stability of DARPin#22 and DARPin#23 using CD-based thermal stability assay (Table 1, FIG. 3). These three DARPins possess an identical amino acid sequence except for two or three amino acid in the N-terminal capping module of their repeat domains. The repeat domains of DARPin #22 and DARPin#23, but not DARPin #21, comprise an improved N-terminal capping module as described herein; i.e. the N-terminal capping module of DARPin#22 and DARPin#23 contain a L residue at position 24 (whereas DARPin#21 contains a M at this position) and an A residue at position 26 (whereas DARPin#21 contains a N at this position); in addition, the N-terminal capping module of DARPin#23 contains a K residue at position 25 (whereas DARPin#21 and DARPin#22 contain an A at this position). Thus, the DARPin#23 comprises an improved N-terminal capping module comprising the amino acid sequence RILLKA (SEQ ID NO:11) from position 21 to 26 as described herein. Surprisingly, these small changes in the N-terminal capping module of DARPins#22 and DARPin#23 resulted in an increase of the Tm value of about 8.5° C. or 7° C., respectively, when compared to DARPin#21. Furthermore, DARPin#22 and DARPin#23 possess an almost identical thermal stability, while their amino acid sequence differs in a single amino acid in the N-terminal capping module of their repeat domains; i.e. the N-terminal capping module of DARPin#22 contains an A residue at position 25 of its N-terminal capping module, whereas DARPin#23 contains a K at this position. Thus, this change of a single amino acid at position 25 of such an N-terminal capping module seems to be well tolerated and to have no effect on the thermal stability.

The thermal stability of DARPin#24 was compared to the thermal stability of DARPin#25 and DARPin#26 using the fluorescence-based and CD-based thermal stability assay (Table 1, FIG. 4). These three DARPins possess an identical amino acid sequence except for three or four amino acid in the N-terminal capping module of their repeat domains. The repeat domains of DARPin #25 and DARPin#26, but not DARPin #24, comprise an improved N-terminal capping module as described herein; i.e. the N-terminal capping module of DARPin#25 and DARPin#26 contain a L residue at position 24 (whereas DARPin#24 contains a M at this position), contain a K residue at position 25 (whereas DARPin#24 contains an A at this position) and an A residue at position 26 (whereas DARPin#24 contains a N at this position); in addition, the N-terminal capping module of DARPin#26 contains an E residue at position 22 (whereas DARPin#24 and DARPin#25 contain an I at this position). Thus, the DARPin#25 and DARPin#26 comprises an improved N-terminal capping module comprising the amino acid sequence RILLKA (SEQ ID NO:11) and RELLKA (SEQ ID NO:12), respectively, from position 21 to 26 as described herein. Surprisingly, these small changes in the N-terminal capping module of DARPins#25 and DARPin#26 resulted in an increase of the Tm value of about 5° C. or 6° C., respectively, when compared to DARPin#24. Furthermore, DARPin#25 and DARPin#26 possess an almost identical thermal stability, while their amino acid sequence differs in a single amino acid in the N-terminal capping module of their repeat domains; i.e. the N-terminal capping module of DARPin#25 contains an I residue at position 22 of its N-terminal capping module, whereas DARPin#26 contains an E at this position. Thus, this change of a single amino acid at position 22 of such an N-terminal capping module seems to be well tolerated and to have no significant effect on the thermal stability.

Overall, the thermal stability of various DARPins can be significantly improved by small changes of the amino acid sequence of their N-terminal capping modules as described herein.

TABLE 1

Tm values of DARPins

|  | Tm [° C.][1] | Tm [° C.][2] |
|---|---|---|
| DARPin #17 | 64.5 | n.d. |
| DARPin #18 | 71.0 | n.d. |
| DARPin #19 | 70.5 | 72.3 |
| DARPin #20 | 73.0 | 74.8 |
| DARPin #21 | n.d. | 56.5 |
| DARPin #22 | n.d. | 65 |
| DARPin #23 | n.d. | 63.5 |
| DARPin #24 | 79.5 | 83[3] |
| DARPin #25 | 84.5 | 89[3] |
| DARPin #26 | 85.5 | 89[3] |

[1]Tm values as determined with the fluorescence based assay in PBS at pH 7.4
[2]Tm values as determined with the CD based assay in PBS at pH 7.4
[3]Tm values are estimates only as no post-transition baseline could be reached n.d.: not determined Example 3: Higher Thermal Stability of DARPins with Improved C-Terminal Capping Modules Thermal stability of DARPins was analyzed with a fluorescence-based thermal stability assay or by CD spectroscopy as described in Example 2.

The thermal stability of DARPin #27 (SEQ ID NO:27 with a His-tag (SEQ ID NO:16) fused to its N-terminus) was compared to the thermal stability of DARPin #28 (SEQ ID NO:28 with a His-tag (SEQ ID NO:16) fused to its N-terminus) using the fluorescence-based thermal stability assay. These two DARPins possess an identical amino acid sequence except for the C-terminal capping module of their repeat domains. The repeat domain of DARPin #28, but not DARPin #27, comprises an improved C-terminal capping module as described herein. The Tm values in PBS pH 7.4 determined for DARPin #27 and DARPin #28 were about 63° C. and about 73° C., respectively. The Tm values in MES buffer pH 5.8 determined for DARPin #27 and DARPin #28 were about 54.5° C. and about 66° C., respectively.

The thermal stability of DARPin #29 (SEQ ID NO:29 with a His-tag (SEQ ID NO:16) fused to its N-terminus) was compared to the thermal stability of DARPin #30 (SEQ ID NO:30 with a His-tag (SEQ ID NO:16) fused to its N-terminus) using the fluorescence-based thermal stability assay. These two DARPins possess an identical amino acid sequence except for the C-terminal capping module of their repeat domains. The repeat domain of DARPin #30, but not DARPin #29, comprises an improved C-terminal capping module as described herein. The Tm values in MES buffer pH 5.8 determined for DARPin #29 and DARPin #30 were about 51° C. and about 55° C., respectively.

The thermal stability of DARPin #31 (SEQ ID NO:31) was compared to the thermal stability of DARPin #32 (SEQ ID NO:32) using CD spectroscopy. These two DARPins possess an identical amino acid sequence except for the C-terminal capping module of their repeat domains. The repeat domain of DARPin #32, but not DARPin #31, comprises an improved C-terminal capping module as described herein. The Tm values in PBS pH 7.4 determined for DARPin #31 and DARPin #32 were about 59.5° C. and about 73° C., respectively.

The invention claimed is:

1. A method of generating a binding protein comprising at least one ankyrin repeat domain, the method comprising the steps of:
   (1) assembling by genetic means a gene encoding an ankyrin repeat domain comprising an N-terminal capping module followed by one or more repeat modules and a C-terminal capping module, and
   (2) expressing said gene encoding said ankyrin repeat domain;
   wherein said N-terminal capping module has an amino acid sequence
   GSDLGKKLLE AARAGQDDEV RILLKAGADV NA (SEQ ID NO:14) or
   GSDLGKKLLE AARAGQDDEV RELLKAGADV NA (SEQ ID NO:15), wherein
      (i) the amino acid residue L at position 24 of SEQ ID NO:14 or SEQ ID NO:15 is optionally replaced by V, I, or A;
      (ii) up to one amino acid of SEQ ID NO:14 in a position other than position 24 or up to two amino acids of SEQ ID NO:15 in other positions than position 24 are optionally exchanged by other amino acids; and
      (iii) G at position 1 and/or S at position 2 of SEQ ID NO:14 or SEQ ID NO:15 are optionally missing.

2. The method of claim 1, wherein up to one amino acid of SEQ ID NO:15 in a position other than position 24 is optionally exchanged by another amino acid.

3. The method of claim 1, wherein the amino acid sequence of said N-terminal capping module is
   GSDLGKKLLEAARAGQDDEVRILLKAGADVNA (SEQ ID NO: 14) or
   GSDLGKKLLEAARAGQDDEVRELLKAGADVNA (SEQ ID NO:15), wherein
   G at position 1 and/or S at position 2 of SEQ ID NO:14 and SEQ ID NO:15 are optionally missing.

4. The method of claim 1, wherein the amino acid sequence of said N-terminal capping module is
   GSDLGKKLLEAARAGQDDEVRELLKAGADVNA (SEQ ID NO:15), wherein
   G at position 1 and/or S at position 2 of SEQ ID NO:15 are optionally missing.

5. The method of claim 1, wherein the amino acid residue R at position 21 of SEQ ID NO:14 or SEQ ID NO:15 is not replaced or is replaced by E.

6. The method of claim 1, wherein the amino acid residue I at position 22 of SEQ ID NO:14 or the amino acid residue E at position 22 of SEQ ID NO:15 is not replaced or is replaced by V.

7. The method of claim 1, wherein the amino acid residue K at position 25 of SEQ ID NO:14 or SEQ ID NO:15 is not replaced or is replaced by A or E.

8. A method of generating a binding protein comprising at least one ankyrin repeat domain, the method comprising the steps of:
   (1) assembling by genetic means a gene encoding an ankyrin repeat domain comprising an N-terminal capping module followed by one or more repeat modules and a C-terminal capping module, and
   (2) expressing said gene encoding said ankyrin repeat domain;
   wherein said ankyrin repeat domain comprises an N-terminal capping module having an amino acid sequence
   GSDLGKKLLE AARAGQDDEV RILLKAGADV NA (SEQ ID NO:14) or
   GSDLGKKLLE AARAGQDDEV RELLKAGADV NA (SEQ ID NO:15), wherein
      (i) the amino acid residue L at position 24 of SEQ ID NO:14 or SEQ ID NO:15 is optionally replaced by V, I, or A;
      (ii) up to 9 amino acids of SEQ ID NO:14 or SEQ ID NO:15 in other positions than position 24 are optionally exchanged by other amino acids;
      (iii) G at position 1 and/or S at position 2 of SEQ ID NO:14 or SEQ ID NO:15 are optionally missing; and
      (iv) the amino acid residue A at position 26 of SEQ ID NO:14 or SEQ ID NO:15 is not replaced or is replaced by H, Y, K, or R.

9. The method of claim 8, wherein the amino acid residues RILLKA from positions 21 to 26 of SEQ ID NO: 14 or the amino acid residues RELLKA from positions 21 to 26 of SEQ ID NO:15 are not replaced.

10. The method of claim 8, wherein said N-terminal capping module comprises the sequence GSX$_1$LX$_2$KKLLE AARAGQDDEV X$_3$X$_4$LX$_5$X$_6$X$_7$GADV NA (SEQ ID NO:5), wherein G at position 1 and/or S at position 2 of SEQ ID NO:5 are optionally missing, and wherein X$_1$ represents an amino acid residue G, A, or D;
X$_2$ represents an amino acid residue G or D;
X$_3$ represents an amino acid residue R or E;
X$_4$ represents an amino acid residue I, E, or V;
X$_5$ represents an amino acid residue L, V, I, or A;
X$_6$ represents an amino acid residue A, K, or E; and
X$_7$ represents an amino acid residue selected from the group consisting of A, H, Y, K, or R.

11. A method of generating a binding protein comprising at least one ankyrin repeat domain, the method comprising the steps of:
 (1) assembling by genetic means a gene encoding an ankyrin repeat domain comprising an N-terminal capping module followed by one or more repeat modules and a C-terminal capping module, and
 (2) expressing said gene encoding said ankyrin repeat domain;
 wherein said ankyrin repeat domain comprises an N-terminal capping module having an amino acid sequence with at least 95% amino acid sequence identity with GSDLGKKLLE AARAGQDDEV RILLKAGADV NA (SEQ ID NO:14) or GSDLGKKLLE AARAGQDDEV RELLKAGADV NA (SEQ ID NO:15), with the condition that the amino acid residue in position 24 in the amino acid sequence of said N-terminal capping module is L, V, I, or A; and wherein position 1 and/or position 2 of SEQ ID NO:14 or SEQ ID NO:15 are optionally missing.

12. The method of claim 11, wherein the amino acid residue at position 21 of said N-terminal capping module is R or E.

13. The method of claim 1, wherein the expression is performed in eukaryotic cells.

14. The method of claim 1, wherein the expression is performed in prokaryotic cells.

15. The method of claim 1, wherein the expression is performed in bacterial cells.

16. The method of claim 1, wherein the expression is performed in a cell-free in vitro expression system.

17. The binding protein of claim 9, wherein the amino acid residue L at position 24 of SEQ ID NO:14 or SEQ ID NO:15 is not replaced.

18. The binding protein of claim 9, wherein the amino acid residue A at position 26 of SEQ ID NO:14 or SEQ ID NO:15 is not replaced.

19. The method of claim 9, wherein the expression is performed in eukaryotic cells.

20. The method of claim 9, wherein the expression is performed in prokaryotic cells.

21. The method of claim 9, wherein the expression is performed in bacterial cells.

22. The method of claim 9, wherein the expression is performed in a cell-free in vitro expression system.

* * * * *

UNITED STATES PATENT AND TRADEMARK OFFICE
CERTIFICATE OF CORRECTION

PATENT NO. : 9,717,802 B2  Page 1 of 1
APPLICATION NO. : 14/947148
DATED : August 1, 2017
INVENTOR(S) : Hans Kaspar Binz et al.

It is certified that error appears in the above-identified patent and that said Letters Patent is hereby corrected as shown below:

On the Title Page

Item (54), "CAPPING MODULES FOR DESIGNED ANKYRIN REPEAT PROTEINS" should read
-- IMPROVED CAPPING MODULES FOR DESIGNED ANKYRIN REPEAT PROTEINS --.

In the Claims

Claim 17, Column 48, Line 18, "claim 9" should read -- claim 8 --.

Claim 18, Column 48, Line 21, "claim 9" should read -- claim 8 --.

Claim 19, Column 48, Line 24, "claim 9" should read -- claim 8 --.

Claim 20, Column 48, Line 26, "claim 9" should read -- claim 8 --.

Claim 21, Column 48, Line 28, "claim 9" should read -- claim 8 --.

Claim 22, Column 48, Line 30, "claim 9" should read -- claim 8 --.

Signed and Sealed this
Third Day of October, 2017

Joseph Matal
*Performing the Functions and Duties of the
Under Secretary of Commerce for Intellectual Property and
Director of the United States Patent and Trademark Office*